(12) United States Patent
Zison et al.

(10) Patent No.: US 6,757,619 B2
(45) Date of Patent: Jun. 29, 2004

(54) SYSTEM AND METHOD FOR ENVIRONMENTAL DATA ACQUISITION

(75) Inventors: Stanley W. Zison, San Diego, CA (US); Joseph Bingham, San Diego, CA (US)

(73) Assignee: Sempra Energy Solutions, Los Angeles, CA (US)

( * ) Notice: Subject to any disclaimer, the term of this patent is extended or adjusted under 35 U.S.C. 154(b) by 0 days.

(21) Appl. No.: 10/214,947

(22) Filed: Aug. 7, 2002

(65) Prior Publication Data

US 2003/0120444 A1 Jun. 26, 2003

Related U.S. Application Data

(60) Provisional application No. 60/312,149, filed on Aug. 13, 2001.

(51) Int. Cl.[7] .......................... G01N 31/00; G06F 19/00
(52) U.S. Cl. ........................ 702/31; 702/32; 700/274
(58) Field of Search ..................... 702/22–28, 30–32, 702/85, 100, 73, 88; 73/863.81–863.83, 863.85; 700/96, 274, 275, 296; 340/632; 204/406, 431; 205/786.5, 781, 784, 784.5; 588/260

(56) References Cited

U.S. PATENT DOCUMENTS

| | | | | |
|---|---|---|---|---|
| 5,206,818 A | * | 4/1993 | Speranza | 702/24 |
| 5,548,528 A | * | 8/1996 | Keeler et al. | 702/22 |
| 5,703,299 A | * | 12/1997 | Carleton et al. | 73/863.83 |
| 5,970,426 A | * | 10/1999 | Mandel et al. | 702/32 |
| 6,212,937 B1 | * | 4/2001 | Hubert et al. | 73/23.2 |
| 6,345,234 B1 | * | 2/2002 | Dilger et al. | 702/24 |
| 6,435,019 B1 | * | 8/2002 | Vojtisek-Lom | 73/118.1 |

* cited by examiner

*Primary Examiner*—Marc S. Hoff
*Assistant Examiner*—Manuel L. Barbee
(74) *Attorney, Agent, or Firm*—Perkins Coie LLP

(57) ABSTRACT

In a data acquisition system and method for real time monitoring of stack gases in a continuous monitoring system, data is collected from sensors and prepared for output to a regulatory agency. The data collected may relate to emissions of oxides of nitrogen, carbon monoxide, and oxides of sulfur, typically from an industrial facility. Sensors in the exhaust gas pathway report data to a programmable logic control device and are then stored in a data storage area. A data acquisition module quantifies the stored emissions data. The quantified emissions data is then sent to a regulatory agency via a communications link.

20 Claims, 32 Drawing Sheets

Fig. 9

SYSTEM AND METHOD FOR ENVIRONMENTAL DATA ACQUISITION

RELATED APPLICATION

The present application claims priority to co-pending U.S. provisional patent application serial No. 60/312,149 entitled ENVIRONMENTAL DATA ACQUISITION SYSTEM AND METHOD, filed on Aug. 13, 2001, which is incorporated herein by reference in its entirety.

BACKGROUND

1. Field of the Invention

The present invention generally relates to air quality management by continuing emissions monitoring systems and more specifically relates to the real-time monitoring of gas pollutant emissions emitted from industrial facilities.

2. Related Art

The requirement for real-time monitoring of stack gas pollutants emitted from industrial facilities is now commonplace, and the physical approach is usually the installation of a conventional continuous emissions monitoring system ("CEMS"). Conventional CEMS are typically electro-mechanical devices made up of four main parts: (1) a sampling system; (2) a data analyzer; (3) a calibration system; and (4) a data logging and communications system.

A conventional sampling system typically consists of a data acquisition system ("DAS") having programmable logic controllers and computer hardware that executes various software utilities to provide data processing. The data analyzer typically consists of additional software utilities to provide data analysis and further processing. A conventional calibration system typically consists of elctro-mechanical sensors and calibrators and corresponding software utilities. Finally, a conventional data logging and communications system usually consists of a database for storing CEMS information and a remote terminal unit ("RTU") for electronically transmitting data to a receiving station such as the local air pollution control authority.

There are two main drivers for conventional CEMS. Of these two, by far the most compelling is the need to demonstrate compliance with environmental legislation such as the Integrated Pollution Prevention and Control ("IPPC"). The second driving factor behind the development of CEMS is increased efficiency of the combustion systems associated with the industrial facility.

The CEMS industry needs improved systems and methods for capturing, processing, analyzing and providing emissions data to regulatory agencies. The present invention provides novel systems and methods to meet this need.

SUMMARY

A data acquisition system is provided as part of a CEMS, whereby the DAS is designed to perform all computations and data manipulations necessary to accept digital data from CEMS and other types of sensory equipment and prepare mass emission summary data for output to a regulatory agency in the form required by the regulatory agency. Such mass emission summary data may be for oxides of nitrogen ("Nox"), carbon monoxide ("CO"), oxides of sulfur ("Sox") or any other gaseous pollutant for which mass emissions information must be computed.

A single application of the program can accommodate one or more physical emitting devices such as an engine, boiler, turbine, furnace, or other. The additional physical devices (beyond the first) can be accommodated by multiple (e.g., sequential or parallel) instantiations of the system or a single instantiation adapted to communication with a plurality of devices.

Each physical device associated with the system correlates to an internal logical device ("DAS device"). Any one DAS device can be associated with any one of the physical devices. For example, if an industrial facility has three CEMS, one monitoring a boiler, one monitoring an engine, and one monitornig a furnace, the first DAS device would be associated with the boiler, the second DAS device would be associated with the engine, and the third DAS device would be associated with the furnace. Other combinations are also acceptable.

In another type of application, the DAS can be used in a cogeneration facility. For example, such a facility might have two physical devices requiring CEMS, namely an engine and a duct burner. The engine can be, for example, a gas turbine (e.g., driving a chiller) with waste turbine-heat recovery used to generate electric power via a steam turbine and generator. When the amount of steam produced with waste heat is inadequate to accommodate the electric power demand (load), duct burners are available (physically located in the engine exhaust duct) to provide supplemental heat for production of steam.

In an installation where the duct burner exhaust pollutants are monitored separately from that of the engine, the DAS can be used in its simplest configuration, namely, the engine is represented by one DAS device and the duct burner by a second DAS device. In some installations, however, the duct burner exhaust is directly and immediately combined with the turbine exhaust, and there is no way to directly measure the composition of the duct burner exhaust. This may be because the burners are physically located inside the turbine exhaust duct or because the duct burner exhaust duct is not amenable to sampling. In this situation, there may be NOx and oxygen analyzers monitoring the exhaust directly downstream of the turbine (Location One Analyzers) and another pair of analyzers (Location Two Analyzers) monitoring the combined exhaust downstream of the duct burners (i.e., monitoring the combined duct burner and turbine exhausts).

Under some circumstances, there may be an additional level of complexity due to the need for a secondary stack. It may be necessary to divert the turbine exhaust to that secondary stack, the main stack being used for duct burner exhaust alone, both turbine and duct burner exhaust may go to the main stack during some part of the time when both are operating, the turbine alone may vent to the main stack (duct burner inoperative), or part of the turbine exhaust may be diverted to the secondary stack when the turbine alone provides more than enough heat for electric power generation. In this situation, information (device status signal) is provided at each sampling time to the internal DAS device by the physical system, regarding on-off status of the turbine and of the duct burner, and regarding where the turbine exhaust is being vented (i.e., the main or secondary stack).

In this situation where the duct burner exhaust cannot be directly monitored, regulatory requirements may make it unacceptable from a regulatory standpoint to mathematically separate the two exhausts in the raw data even where the inherent nature of the data themselves would allow it, or it may be physically impractical or impossible to correctly do so. In such cases, the DAS devices may be configured to analyze the combined exhaust of the engine and duct burners and compute the required mass emission rates. For example, the first DAS device may be assigned directly to the turbine, and it analyzes the exhaust of the turbine alone, whether that is directed to the main or secondary stack. The second DAS device applies only to the turbine when its exhaust is directed to the main stack. And a third DAS device can represent the main stack itself. Then, to obtain duct burner emissions, the second DAS device output (turbine only when directed to the main stack) is subtracted from the third DAS device output (turbine plus duct burners if operating), to result in the quantification of the mass emissions from the duct burners alone.

BRIEF DESCRIPTION OF THE DRAWINGS

The details of the present invention, both as to its structure and operation, may be gleaned in part by study of the accompanying drawings, in which like reference numerals refer to like parts, and in which:

FIGS. 7–9 are graphical user interface windows illustrating example RTU application screen shots according to an embodiment of the present invention;

DETAILED DESCRIPTION

Figure 1A:
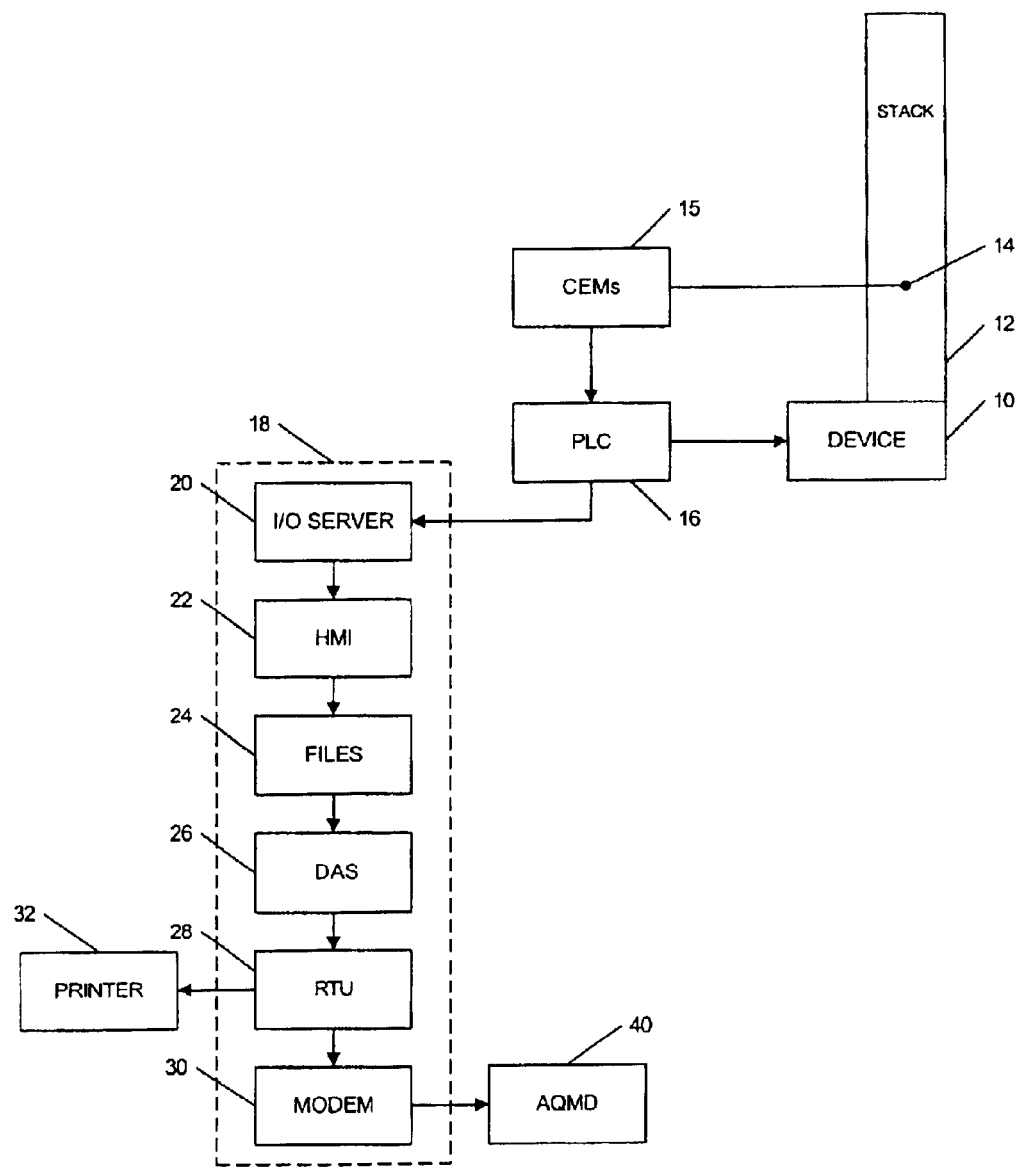
FIG. 1A is a high level block diagram illustrating an example air quality management system according to an embodiment of the present invention.

Certain embodiments as disclosed herein provide for systems and methods for processing air quality management emissions information and providing that information to an air quality management district or using that information for facility optimization and improvement of facilities management. For example, one method as disclosed herein allows for an air quality management system to receive emissions data from a plurality of deployed sensors and derive statistics for individual components and devices of the facility being monitored.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

In one embodiment, the data acquisition software (DAS) of the present invention requires three kinds of input. One consists of a set of constants and program control information. This includes bias adjustment factors developed during the most recent relative accuracy test audit (RATA), constants relating to fuel combustion (higher heating value; and F factor, the volume of stack exhaust gas flow per unit volume of gaseous fuel combusted), and types of reports to be prepared.

The second type of data provides stack gas composition and fuel information. This file provides periodic data for liquid fuel flow, gaseous fuel flow, gaseous fuel pressure and temperature, NOx or other pollutant concentration in the exhaust, and oxygen content of the exhaust.

The third type of data may be called an alarm log or event log, and contains information about when certain events begin and end, which events bear upon the way data must be processed or upon the validity of the data. For example, during calibration, the stack data do not represent actual emissions from the monitored device. The CEMS gas sampling probe during calibration does not sample stack gas. Rather, it samples a standardized gas, and the concentration data gathered during calibration periods must not be taken to represent stack conditions. In order to avoid processing calibration data as if they do so characterize emissions, information must be provided to the DAS specifying when calibrations begin and end. Such information, which is included in the event log, allows the DAS to properly handle the calibration period as a maintenance period of as missing data.

Similarly, the DAS must receive information about when a communication failure, calibration failure, or power failure begins and ends so that the data during such periods can be handled as invalid, and so that the DAS can again begin handling the stack data when conditions have returned to normal.

Every day, when emission data are transmitted to the Air Quality Management District (AQMD or "the District"), they require that part of each record indicating total daily NOx emissions for the particular device also provide nine bits of device status information. Those bits represent the following:

Bit Meaning if Bit is set to "true" of "1"

1 Valid data were obtained all day.

2 At least one calibration was attempted during the day.

3 The monitoring system (CEMS) was off at least once during the day.

4 An alternate data acquisition method was used.

5 The CEMS was out of control at least once.

6 More than one fuel was used during the day.

7 Concentration measured at less than 10% of span was reported as 10% of span.

8 Concentration measured at less than 10% of span was reported at actual value.

9 Device non-operational for the entire day.

With reference to FIG. 1A, an overall system diagram which includes an embodiment of the invention is shown. One or more devices 10 which are the subjects for environmental emissions management may have an exhaust pathway or stack 12 with a CEMS gas sampling probe 14. The sampling probe 14 is connected to a CEMS device 15 that produces analog signals to a programmable logic control (PLC) 16. The PLC 16 converts the analog signals into digital signals readable by an input/output (I/O) server 20 of a computer or personal computer device 18.

The data received from the PLC 16 is stored in a stack data file on the PC 18 on a file storage device 24. The device 10 also has a connection to the PLC 16 providing alarm or event data, which are forwarded to the PC 18 where the event data are stored in an event log file on the file storage device 24. The RATA data are also stored on the file storage device 24.

The RTU module 28 running on the PC 18 is capable of reading the files stored on the file storage device 24. The RTU module 28 may conduct some preparation of the input data files before the RTU module 28 calls the DAS module 26 which reads the input files for processing. After processing, the DAS module 26 returns control to the RTU module 28, which may print reports on a printer 32, and forward data to the AQMD 40 by modem 30 or other connection or network device.

DAS Subroutines

Figure 1B:
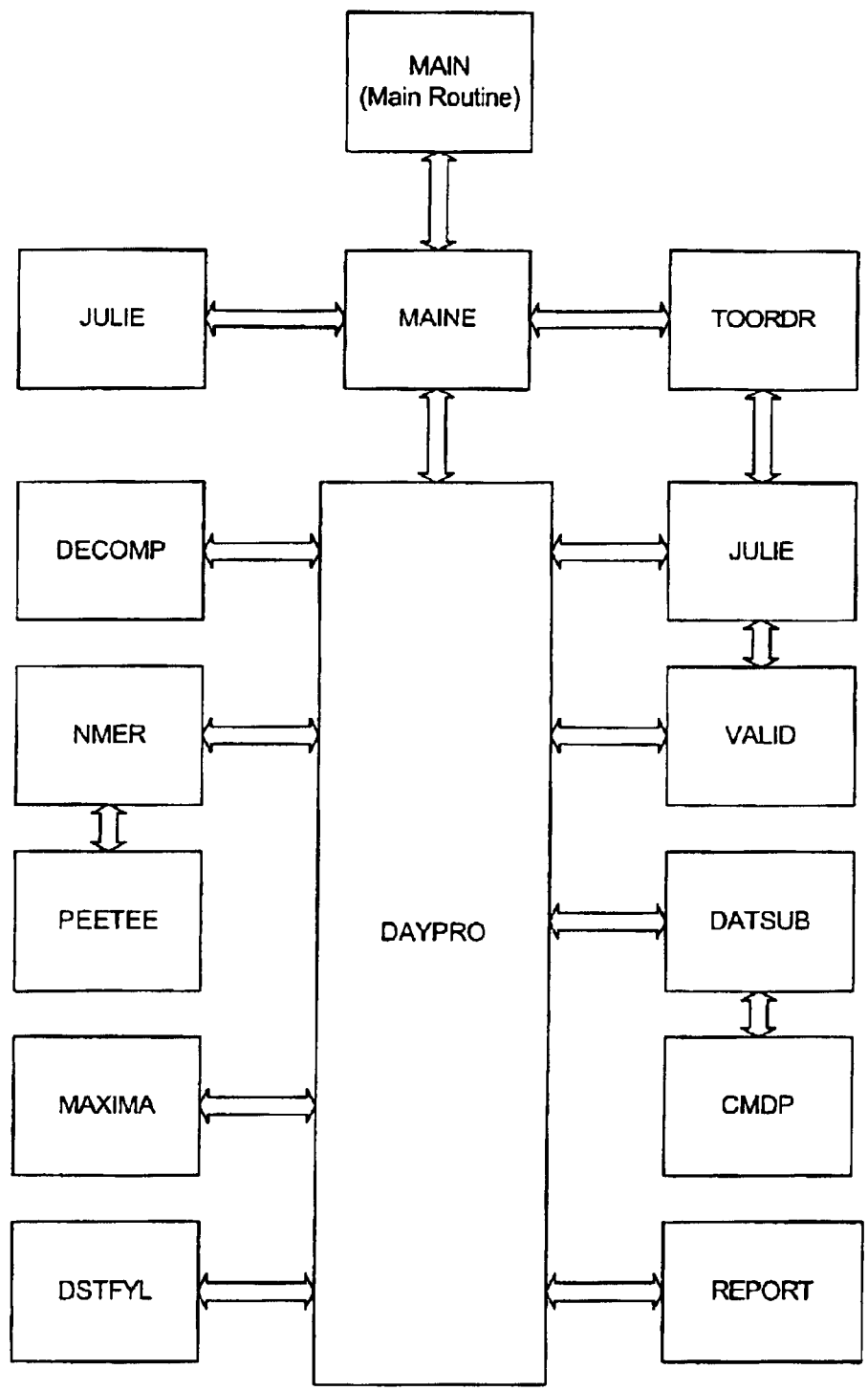
FIG. 1B is a block diagram illustrating an data acquisition system according to an embodiment of the present invention.
Figure 2:
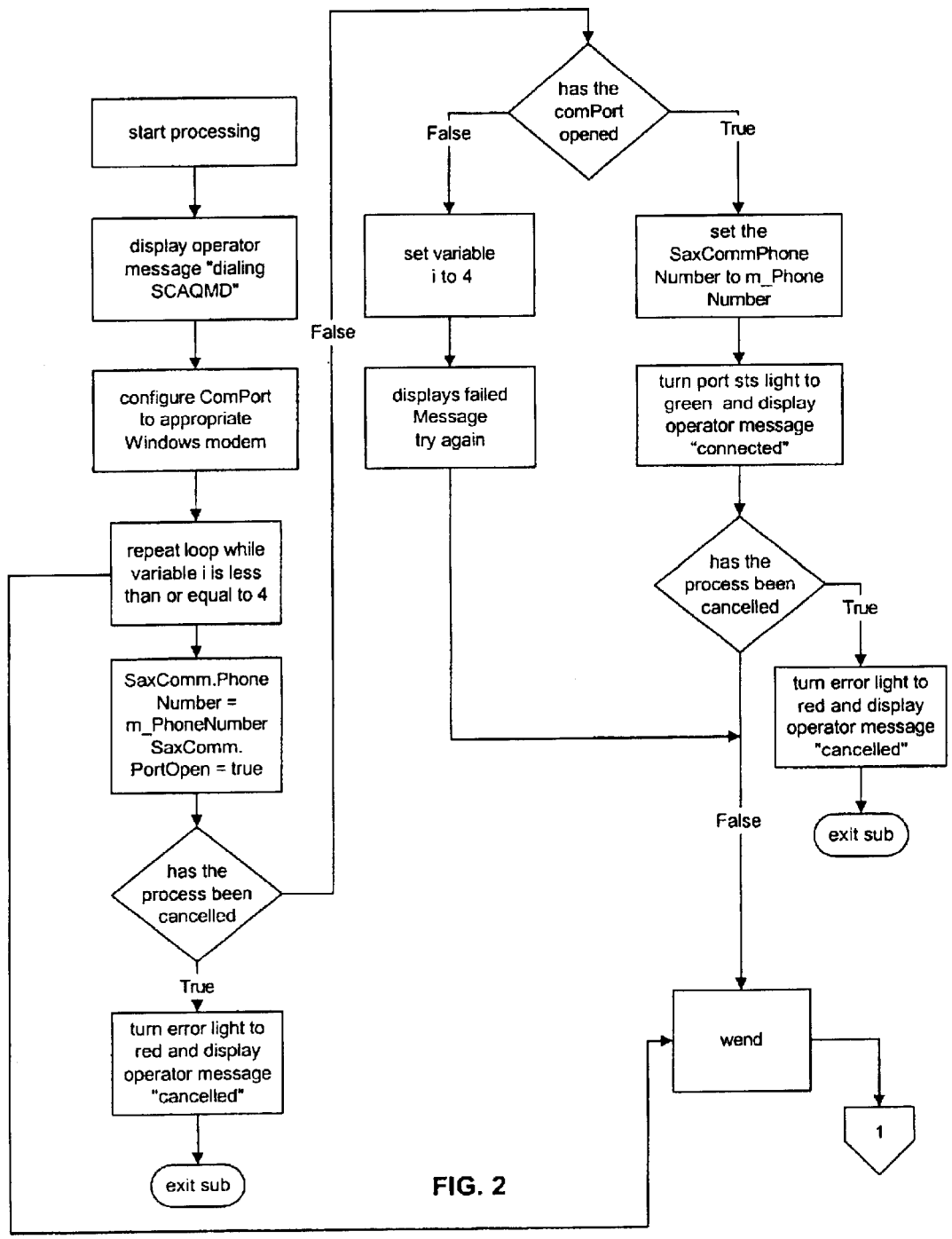
FIGS. 2–5 are flow diagrams illustrating example processes for implementing a message label and alarm annunciation method according to an embodiment of the present invention.

With reference to FIG. 1B, a block diagram illustrating the modules of the data acquisition system (DAS) 26 of one embodiment is shown. In this embodiment, the source code for the DAS program 26 is written in FORTRAN-77, consisting of a main routine called MAIN and a number of subroutines. Descriptions of the basic functions of the main routine and subroutines are presented below in alphabetical order.

CMDP

Subroutine CMDP is used in conjunction with Subroutine DATSUB and determines the beginning and ending times of each discrete missing data period using Subroutine JULIE. A missing data period is defined as any continuous sequence of hours in which NOx concentration, or stack flow, or both, are invalid. CMDP is called, before DATSUB attempts the first data substitution, to initially set up the beginning and ending times for all missing data periods, and is then called at the conclusion of each data substitution pass by DATSUB to determine if any missing data periods remain. If so, CMDP establishes the beginning and ending times of each remaining missing data period, and DATSUB then makes its next data substitution pass.

DATSUB

Subroutine DATSUB performs all data substitution functions for the DAS 26. It reads data from MAXIM.DAT, a file that Subroutine MAXIMA had updated in every earlier DAS 26 invocation, and computes the average percent data availability for the NOx and oxygen analyzers from all prior days back to the 365$^{th}$ prior day if so long a period of data is available. It also searches backward, similarly beginning with the date of the first of the three days to be processed, and finds the 30-day, 365-day, and lifetime maxima for NOx concentration, liquid fuel-based stack flow and NOx mass emission rate, and gaseous fuel-based stack flow and NOx mass emission rate.

Next, in preparation for data substitution, DATSUB calls Subroutine CMPD which finds the beginning and ending hours for each unbroken missing data period. DATSUB and CMPD take each period in which there is a continuum of missing NOx concentration, and/or missing stack flow, and/or both, and defines it as a single missing data period. Accordingly, a single missing data period may contain exclusively hours where only NOx concentration is missing, exclusively where stack flow is missing, where both are missing for all hours, or may involve any combination of the three. For those periods in which only one or the other of NOx concentration or stack flow is missing, it uses the corresponding percent data availability to determine the allowable data substitution algorithms. Where a single period involves any one or more hours where both are missing, it chooses the lesser of the two percents data availability for all hours of missing data. But subsequently, in the process to be described, it then performs the proper data substitution procedure for missing NOx concentration if that alone is invalid, or stack flow if that alone is invalid, or NOx mass emission rate if both NOx concentration and stack flow are invalid.

In its first invocation by DAYPRO, DATSUB executes an algorithm in which the percent data availability determines the first type of data substitution attempted for stack flow. For example, if the percent data availability for the oxygen analyzer is at least 95%, then per District rule, 1N data substitution may be performed if the missing data period for stack flow does not exceed 24 hours and if the 24 hours preceding, and the 24 hours following, the missing data period are valid (or have already been themselves substituted). Since the District rule requires data transmission of the previous day's data by 5 PM, and it is desirable that some time be allowed in case of problems with processing, the DAS considers a total of 62 hours of data. This encompasses 24 hours on the first day, 24 hours on the second (the day whose data must be reported) and 14 hours on the third day—the day of reporting. This brings processing to 2 PM on the third day, allowing 3 hours for problem resolution. This also means that the routine can substitute up to 14 missing hours at the end of the second day.

In this example case, where 1N substitution is proper (as a representative example of the various data substitution processes performed by DATSUB), this routine attempts to perform 1N substitution for each missing data period, one at a time, proceeding chronologically through all 62 hours. Upon completing its pass through the entire 62-hour period, and having marked each period for which data substitution was successful, DATSUB checks to see if at least one substitution has indeed been accomplished. If so, it again invokes CMDP to develop a new set of beginning and ending hours for the remaining unsubstituted missing data periods. Then DATSUB again attempts to perform 1N substitutions, and this iterative process of substituting, marking, and redefining the set of missing data periods continues until no further substitutions can be made using the 1N procedure. At this point, all missing stack flows may have been substituted, or some or all may remain. If any unsubstituted missing data periods do remain, then a 30-day, 365-day, or lifetime maximum is substituted per District rule. Once done, DATSUB again invokes CMDP, and returns to attempting 1N substitution. This algorithm continues until all missing stack flow data have been substituted. The algorithm is aggressive in that it performs data substitution in a way that meets District requirements, but also minimizes the total data-substituted mass emissions.

DATSUB is also called by DAYPRO in a second pass, for periods in which both NOx concentration and stack flow are invalid. In this case, it uses the lesser of the percents data availability (for NOx and oxygen analyzers) and determines which types of data substitution are proper per District rule. But like stack flow data substitution already described, it uses an aggressive algorithm which attempts to use 1N substitution where possible, or performs a 3-hour substitution if that is possible. If not, then it attempts a 30-day maximum substitution, and so forth, always returning to attempt the most favorable legitimate data substitution procedure after each time a missing data period is substituted.

DAYPRO

This is the central subroutine of the DAS. It is called by MAINE for each minute of stack/fuel data for each of the three days, and processes it to completion by calling a number of other subroutines. First, DAYPRO checks to see if the data received is the first minute of the day. If so, it calls VALID to develop a summary internal event log (stored in memory) from the external detailed (input) event log (see description of VALID) and then it uses the internal event log to develop a DAS status word array, S, for each second of the day (86,400 elements), where each such DAS status word reflects whether certain special operating conditions (SOC) were in effect during a given second of the day. The special operating conditions include monitored device offline, CEMS being calibrated, CEMS maintenance period, general CEMS calibration failure, NOx analyzer span calibration failure, NOx analyzer zero calibration failure, oxygen analyzer span calibration failure, oxygen analyzer zero calibration failure, power failure, or communication failure. With B being set to 1 if the SOC is in effect for the particular time under consideration, and 0 if not, the DAS status word, S, is given by the sum over 10 SOCs as follows (n ranges from 0 to 9):

$$S=\Sigma B 2^n$$

The benefit of using the DAS status word derives from the fact that the external event log, which is one of the input files to the DAS 26, may contain information that is out of chronological order, events sequentially listed in that event log may temporally overlap to various degrees, or events may relate to prior events (like calibration failure messages). Thus each value of S encompasses all SOCs for a particular point in time, the information about which may be scattered throughout the external event log. And S provides a unique value for all possible combinations of the 10 SOCs. Accordingly, after every second of the day and every event contained in the internal event log has been processed, the result is array S, each element of which contains all necessary information about the operating condition of the CEMS and the monitored device for each second of the day. Further, the values of S may be decomposed as each sub-minute observation is being processed to indicate whether each SOC is ongoing or not at the time of the observation.

For each minute of the day, DAYPRO determines the Julian time of each stack/fuel observation by calling JULIE, and then calls DECOMP to decompose the DAS status word corresponding to that same time. The sub-minute observations contained within the one minute of data transferred to DAYPRO are stored in an array called QUALS accommodating up to 60 elements, and each such observation is evaluated for validity using the status information from DECOMP. Invalid values in QUALS are changed to −99.99, a code used throughout the remaining program to connote non-validity, and used, for example, to trigger District-required data substitution.

DAYPRO computes one-minute average values from valid data for all variables needed to compute NOx mass emissions, i.e., liquid fuel flow rate, gaseous fuel flow rate, gas pressure and temperature for correcting flows to STP, stack NOx concentration, and stack oxygen concentration. These are stored in an array called QUALM with dimensions 6×1440. Then, if the minute being processed represents the end of the day, DAYPRO computes 15-minute averages (weighting each sub-minute value equally) and stores these in an array called QUALF of dimensions 6×96. DAYPRO computes hourly averages from equally-weighted 15-minute averages in QUALF, tracking the validity of these averages using 15-minute and hourly validity flag arrays. The hourly averages are stored in an array called QUALH, with dimensions 10×24. The increase in the first dimension from 6 to 10 is to later accommodate, in QUALH, the computed liquid and gaseous fuel stack flows and NOx mass emssion rates for each hour.

During the process of computing the various averages, QUALM, QUALF, and QUALH, DAYPRO also performs a number of other requirements under District rule, including setting the nine-bit District status word for the day, evaluating raw data observations to determine which are outside of the acceptable range of 10%–95% of span and taking the necessary steps where they are so, and determining which 15-minute, and consequently which 1-hour data, are valid. To accomplish the latter, DAYPRO looks at, for example, whether at least one successful calibration was performed for the day for NOx and for oxygen, and also analyzes and accounts for maintenance periods per District rule.

Once DAYPRO has developed hourly averages in QUALH, it calls NMER to compute the stack flows per hour due to gaseous fuel combustion and due to liquid fuel combustion where all five required variables have valid hourly averages. These variables are liquid fuel flow, gaseous fuel flow, gaseous fuel temperature, gaseous fuel pressure, and stack oxygen concentration. DAYPRO next calls DATSUB to perform stack flow and NOx concentration data substitution. NMER is called again, this time to perform NOx mass emission rate data calculation. Such calculation is not done in the first call to NMER because substituted hourly average stack flows must first be used with valid NOx concentrations to calculate NOx mass emission rates. NOx mass emission rate substitution is properly done only where both NOx concentration and stack flow hourly averages are invalid. Next, DAYPRO calls DATSUB for the second time to perform data substitution where NOx mass emission rates could not be computed due to invalid data.

Next, DAYPRO checks to see if the current day is the middle one of the three (i.e., the day whose data must be reported to the District) and, if so, it calls Subroutine MAXIMA. MAXIMA examines the hourly averages for NOx concentration, stack flow due to gaseous fuel combustion, stack flow due to liquid fuel combustion, and the NOx mass emission rates due to combustion of the two fuel types. It finds the hourly maxima for the day based only on unsubstituted data, plus it computes the number of on-line hours for the NOx and oxygen analyzers and the monitored device itself. The maxima and on-line hours are written to a direct-access file called MAXIM.DAT for subsequent DAS use.

Finally, if the day is the third of three, DAYPRO calls Subroutine REPORT and Subroutine DSTFYL to prepare documentation reports; and the daily, monthly, or quarterly file to be transmitted electronically to the District, respectively.

DECOMP

The DAS status words described under DAYPRO identify all SOCs in effect for each second of the day being processed. Accordingly, for example, if the monitored device is offline at the same time as a calibration is ongoing, both during the course of a longer maintenance period, the DAS status word will be computed to include all three such SOCs. During subsequent processing of each sub-minute stack/fuel record, the DAS status word corresponding in time to that stack/fuel record must be decomposed to determine whether that sub-minute record represents valid or invalid data. For example, during a calibration, all stack/fuel records must be recognized by the DAS as such, amd not interpreted as stack gas quality data. DECOMP decomposes the appropriate DAS status words and allows DAYPRO to handle the input stack/fuel data as necessary. Also, decomposing the DAS status word allows certain other specific actions to be taken as appropriate-such as resetting to zero some low but non-zero raw data NOx concentration, where the monitored device is offline and the District definition of offline is also met.

DSTFYL

Subroutine DSTFYL prepares the specific files required to be transmitted to the District by 5 PM each day for the prior day, and also prepares the files for monthly and quarterly reporting.

JULIE

Subroutine JULIE is called by many others in the program and is used to convert every date and time stamp (such as the date/time of a stack/fuel record or the end of a calibration period) to a single value that can readily be compared with other similarly converted event date and time stamps, and which can be conveniently processed by the program. To do this, JULIE accommodates the transition to year 2000 and leap years, and computes the time between any specific date/time stamp and the midnight between Dec. 31, 1994 and Jan. 1, 1995. These values, in seconds, are here called the Julian time of the particular event.

MAIN

MAIN is the main routine of the program. It serves primarily to provide two optional modes of operation. One mode is the use of the DAS for single-pass, routine data processing in compliance with SCAQMD (District) RECLAIM Rule 2012. Here, three days of data are processed whenever the program is invoked, namely the current day plus two prior days, the middle day of the three being the day for which results must be transmitted to the District. Three days are processed in order to allow for 1N data substitution of up to 24 missing hours.

In another mode, MAIN provides for historical data reprocessing. In this mode, the DAS is simply invoked repeatedly between two preset dates. Otherwise, processing is the same as in single-pass routine data processing.

MAINE

Subroutine MAINE provides some basic control, input, and administrative functions. It reads certain constants, such as bias adjustment factors, fuel constants, and report preparation options. Then it sets up the outer-most loop of the program, to step through all devices (monitored equipment such as engines, boilers, or turbines). Within this loop, it examines each stack/fuel input file required by the program for each device. It calls subroutine TOORDR to sort the input files and assure they are subsequently processed by the DAS 26 in chronological order. Using Subroutine JULIE, it examines the first file to determine the sampling interval (time between stack gas/fuel flow sampling events) and checks subsequent files to assure that the sampling interval remains constant. The program also checks to verify that such sampling interval is the same as that established at the most recent RATA (relative accuracy test audit), as the interval must remain as so-established, at least until the next RATA under District rules. MAINE next reads one minute's worth of stack/fuel data and adjusts the NOx and oxygen concentrations by applying the bias adjustment factors obtained from the most recent RATA. Finally, for each such minute of data, MAINE calls the central subroutine of the DAS 26, called DAYPRO, to perform all of the remaining data processing.

MAXIMA

The MAXIMA routine is called by DAYPRO exclusively for day two of the three being processed, to update a file called MAXIM.DAT. This file contains, for each monitored device, the daily maxima for unsubstituted NOx concentration, stack flow and NOx mass emissions due to liquid fuel combustion, and stack flow and NOx mass emissions due to gaseous fuel combustion. It also stores the on-line hours for the NOx and oxygen analyzers and the monitored device itself.

NMER

Using a District-specified equation, NMER computes the stack flow due to liquid or gaseous fuel combustion and then the NOx mass emission rate based on the stack flow and the stack NOx concentration. NMER is called twice by DAY- PRO. The first time, NMER computes stack flows for all hours having valid fuel and oxygen data. DAYPRO then calls DATSUB to perform stack flow and NOx concentration data substitution and, once that is done, calls NMER for the second time to compute NOx mass emission rates for all valid and substituted stack flows and NOx concentrations.

PEETEE

Certain gas flow-metering devices provide flows corrected to STP based upon a reference temperature and pressure inputat installation or calibration times. Since the actual pressure and temperature of the process fuel gas change over time, the flows reported by such devices need correction for the differences between reference and actual gas pressures and temperatures. PEETEE is a function subprogram to provide such correction.

REPORT

Upon completion of processing, Subroutine REPORT prepares documentation reports for the facility's records, as required by the District.

TOORDR

The DAS 26 is configured so that the names of the stack/fuel input files are themselves to be read in by way of a computer data file. The names of the stack/fuel input files need not be presented in chronological order as this subroutine is used to examine the data in each stack/fuel input file and establish the input file chronology. Once TOORDR is executed, the DAS 26 has information that allows it to read stack/fuel data from a large number of files chronologically regardless of their names or the order in which they have been specified.

VALID

Subroutine VALID processes the external event log and creates the internal summary event log from which the array of DAS status words is developed. The DAS status word is discussed under DAYPRO, above. VALID performs its tasks using an input file containing records consisting of date and time stamp and an alphanumeric code for the various events that are of importance in processing the data, i.e., special operating conditions, SOC. For example, a record, with fields representing date and time, might indicate that calibration has begun. Another, with its date and time fields, would then indicate that calibration has ended. Still another record might signal that a maintenance period has begun, and another might indicate that the monitored device had been brought off line—which could occur during the maintenance period or the calibration period.

The codes interpreted by VALID to signal start and stop times of various special operating conditions are arbitrary and are determined by the programmer setting up the CEMS data logging system. That system can be, for example, Wonderware InTouch or other similar commercial program capable of receiving data from the programmable logic controller that, it turn, accepts analog current and voltage signals from the CEMS and monitored device and converts those signals to digital form.

VALID uses two logical-variable flag arrays and an integer array with which to track the SOCs. One logical array is called LFLAG and the other is FLAG. LFLAG has 10 elements representing the 10 SOCs. For example, element 1 of the 10 might represent monitored device offline, and element 2 might represent calibration. The values of the 10 elements are set by the DAS 26 and written to a computer data file at midnight at the end of the first day of the three being processed, and these flags represent the status of the 10 SOCs as of that time—"true" meaning the SOC is not in effect and "false" meaning the converse. The next time the DAS 26 is invoked, LFLAG is read back in to initialize the status of the SOCs since, in that next invocation, the starting time of the first day of three is that same midnight ending the first day in the prior invocation. FLAG, in contrast, is a 10×250 element array where the 10 dimension again represents the various SOC's with the same sense as LFLAG, but for each of up to a 250-"row" chronology. In each such row used, of the ten flag values, all have a value of true but one—the specific location along the 10 dimension identifying which SOC is involved. FLAG is used in conjunction with a 2×250 element integer array called VALYOU which stores the beginning and ending times for each SOC, again the 250 dimension representing the chronology of events.

To develop the internal event log and DAS status word array described earlier under DAYPRO, VALID reads each record from the external event log, checks to see if it contains an alphanumeric code signaling an SOC and then, if so, checks to see if the code represents the beginning or ending of that SOC. In addition, certain SOCs do not have a beginning and end, but represent a discrete event, such as calibration failure. When VALID finds an external event log record signaling the beginning of an SOC, it moves forward one step along the 250 row chronology, and resets the corresponding element of 10 from true to false. At the same point, VALID calls JULIE to obtain the Julian time of the beginning of the SOC and inserts that into the corresponding chronological element 1 (of 2) of VALYOU. If the external event log record signals the end of an SOC, then VALID searches backward through those rows (of 250) of FLAG already used, to locate the SOC's beginning. Once found, VALID calls JULIE and inserts the Julian time of the end of the SOC into element 2 of VALYOU. In case of a calibration failure, VALID implements the District rule by searching back to find the beginning of the failed calibration and resets element 1 of VALYOU to the beginning of the hour in which the failed calibration ended. Whenever a valid calibration occurs, VALID not only proceeds as already described in setting the elements of FLAG and VALYOU for that calibration, but also searches backward to the last failed calibration and sets element 2 of VALYOU (the end of the failed calibration) to the end of the hour in which the subsequent successful calibration ended.

VALID continues in this way until the entire external event log has been processed. At that point, it again checks all second elements of VALYOU within the resulting chronology and, for any SOCs with a beginning time but no ending time, it sets the ending times to the midnight at the end of the day. Finally, VALID then uses the internal event log so created, and consisting of as many rows as needed of the 250 available to establish a complete chronology, to compute the DAS status word for every second of the day, as described under DAYPRO.

RTU Method Steps Performed

With reference to FIGS. 2–5, a flow chart showing the steps performed by a SendFile procedure provided in the RTU module 28 is shown. The steps specifically illustrate a message label and alarm annunciation method performed by the system.

Figure 3:
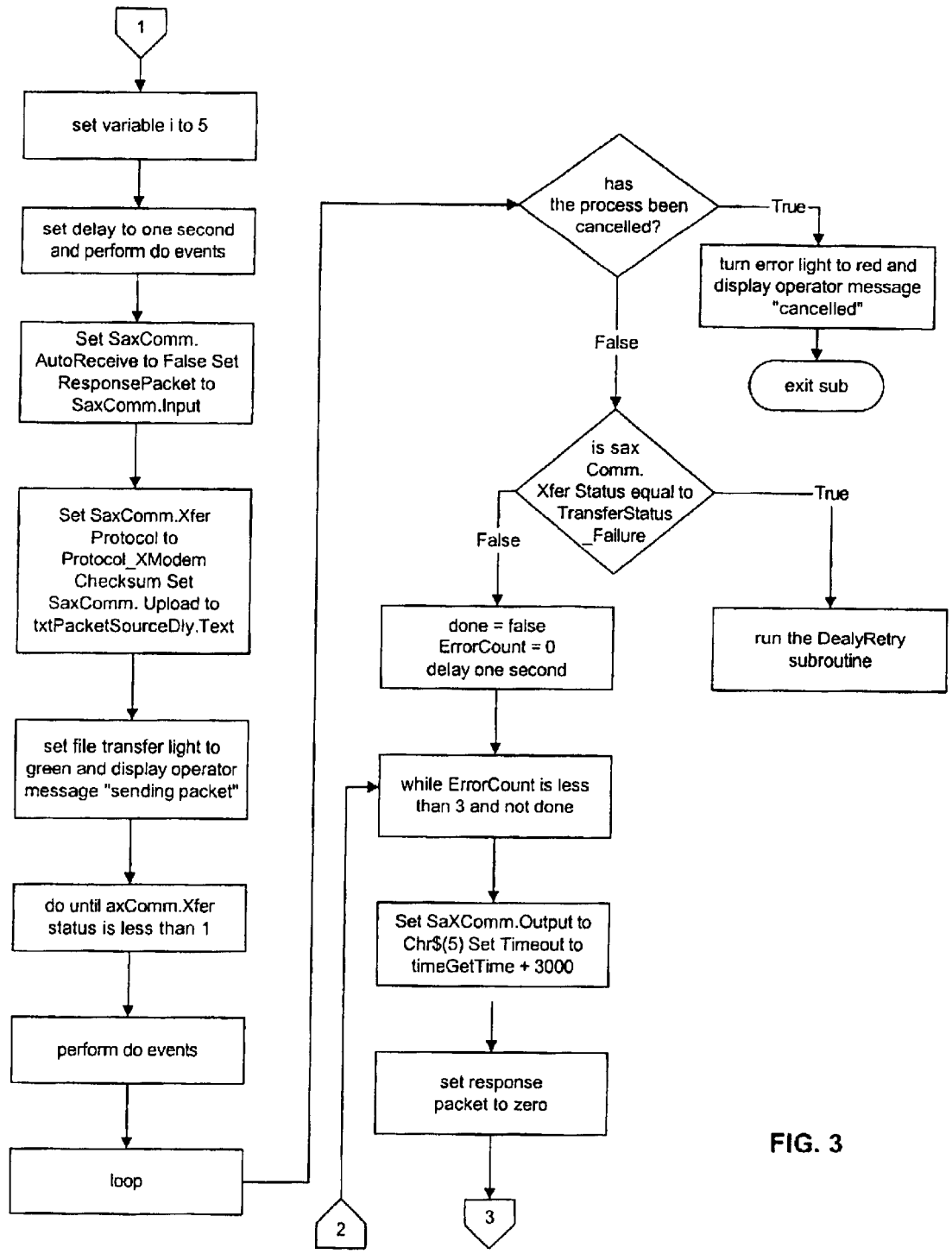
Figure 4:
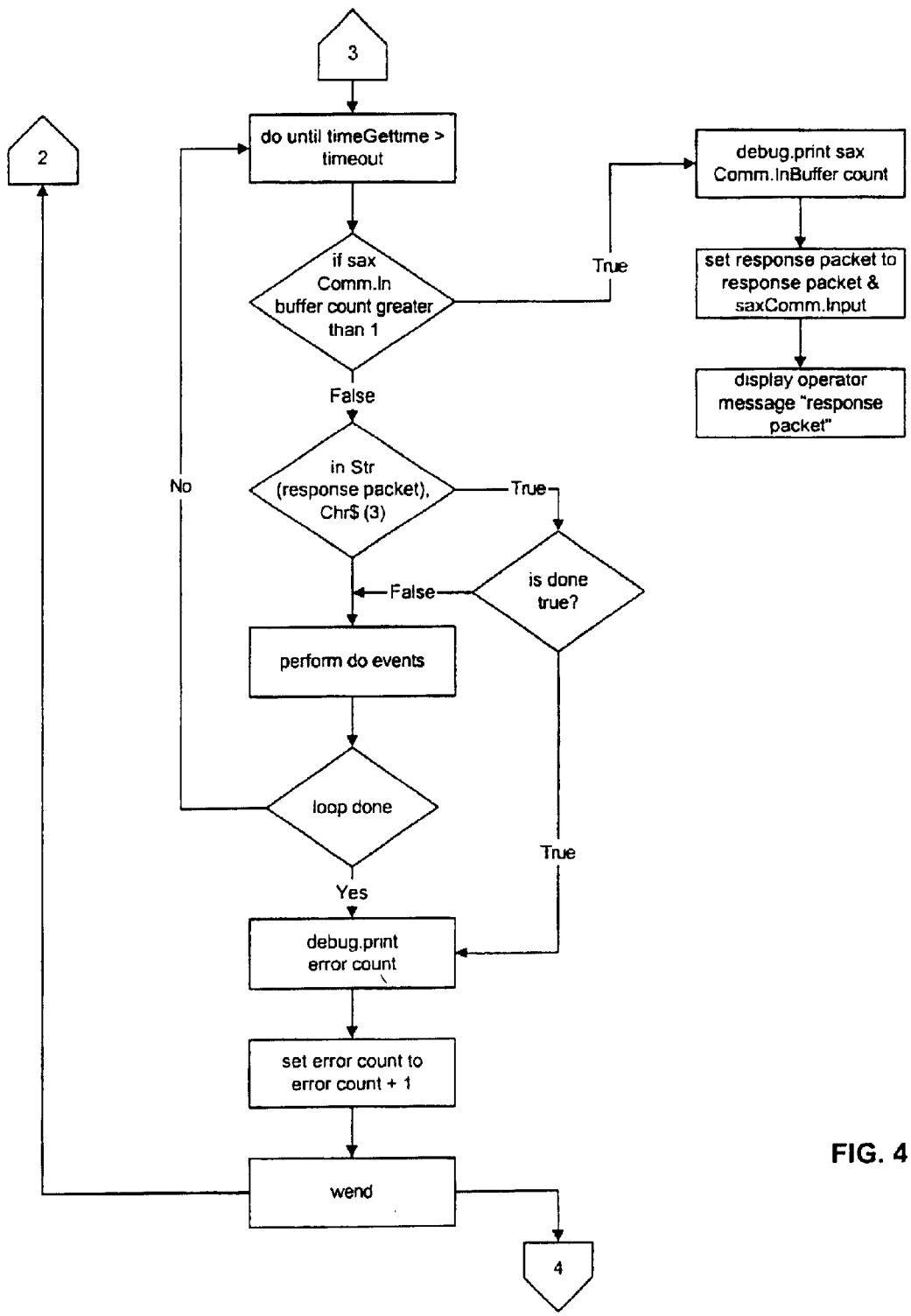
Figure 5:
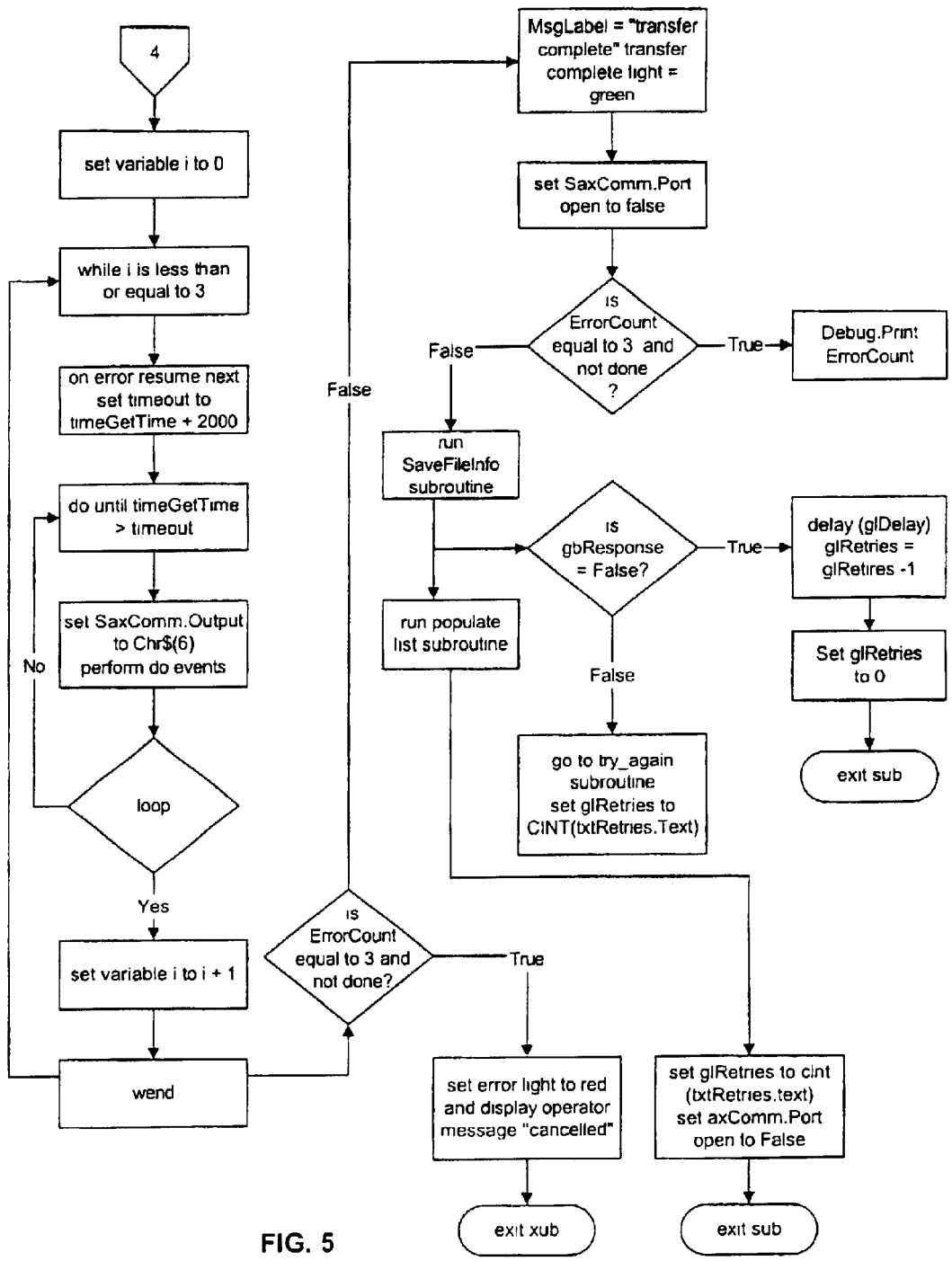

With reference to FIG. 3, the steps of a method for modem 30 setup and transmission log writing is shown. The RTU module 28 performs a set MsgLabel command in the modem to "Dialing SCAQMD." The appropriate modem communications port is configured. The communication port is tried five times. If unsuccessful then the MsgLabel is set to "Failed Five times, Will try again in X minutes." The RTU 28 calls a DailyRetry subroutine and an error light set to red. If successful then the AQMD phone number is dialed. Saxcomm object parameters are prepared to perform a file transfer using the XModem Checksum protocol.

The target file is uploaded to the AQMD. The file transfer light is set to green and the MsgLabel is set to "Sending Packet". The events are performed until the transfer status is less than 1. This lets the user know that the file transfer is complete.

If the process is canceled then the error light is set to red, and the MsgLabel is set to "Canceled." The subroutine is cancelled.

If there is an error in the file transfer then the DailyRetry subroutine is called.

If the file transfer is complete then send Chr$(5) ENQ with a three second delay up to three times. The RTU 28 saves the response packet from SCAQMD. If Char$(3) is received then transmission is complete.

Chr$(6) ACK is resent with a three second delay up to three times. This will tell the AQMD to store the sent data. The MsgLabel is set to "Transfer Complete" and the transfer complete light is set to Green. The communications port is closed.

If the AQMD response was BAD, then wait a preset amount of time and the try to retransmit again.

Figure 6:
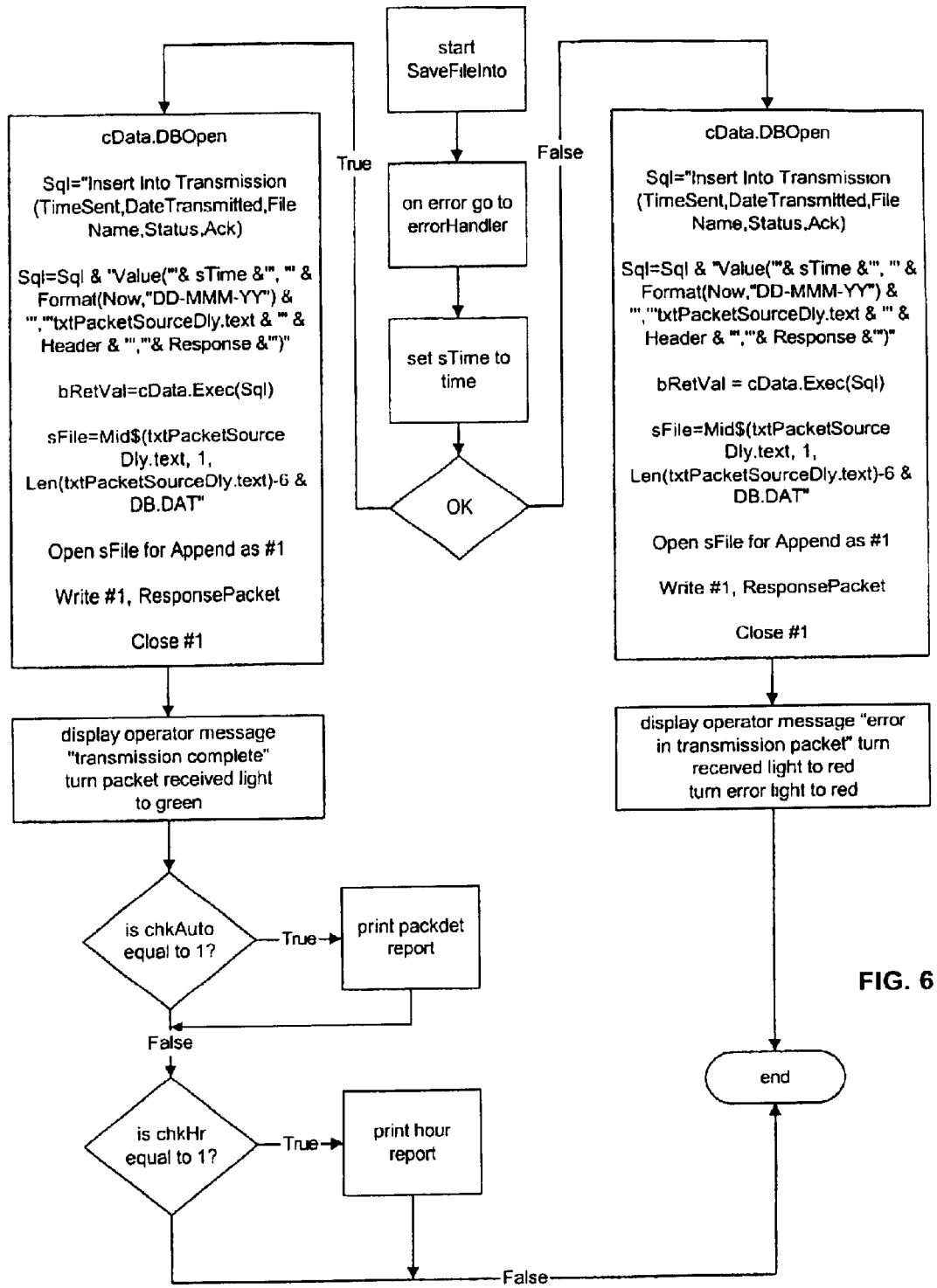
FIG. 6 is a flow diagram illustrating a example process for printing daily and hourly reports according to an embodiment of the present invention.

The RTU 28 also includes a Save FileInfo procedure, which performs the steps illustrated in FIG. 6. If the AQMD response packet was OK, then a database is opened and the response information is written as well as the date, time and file name to the database. The system appends response information to daily file, and prints daily and hourly reports.

If the AQMD response packet indicates BAD, then the system opens the database and writes response information as well as the date, time and file name to the database. The system appends the response information to the daily file.

Figure 7:
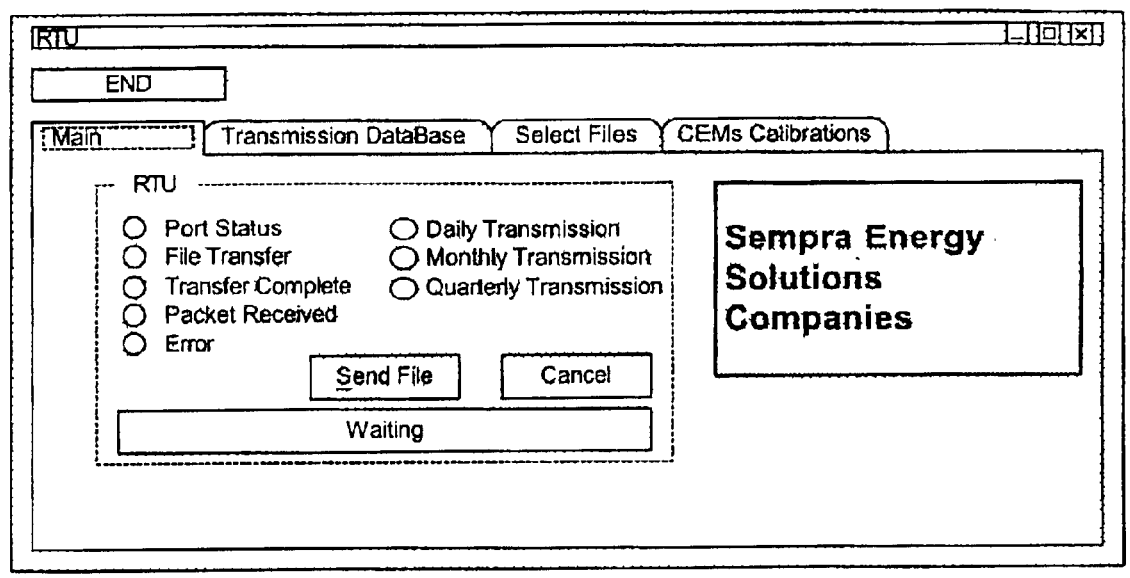
Figure 8:
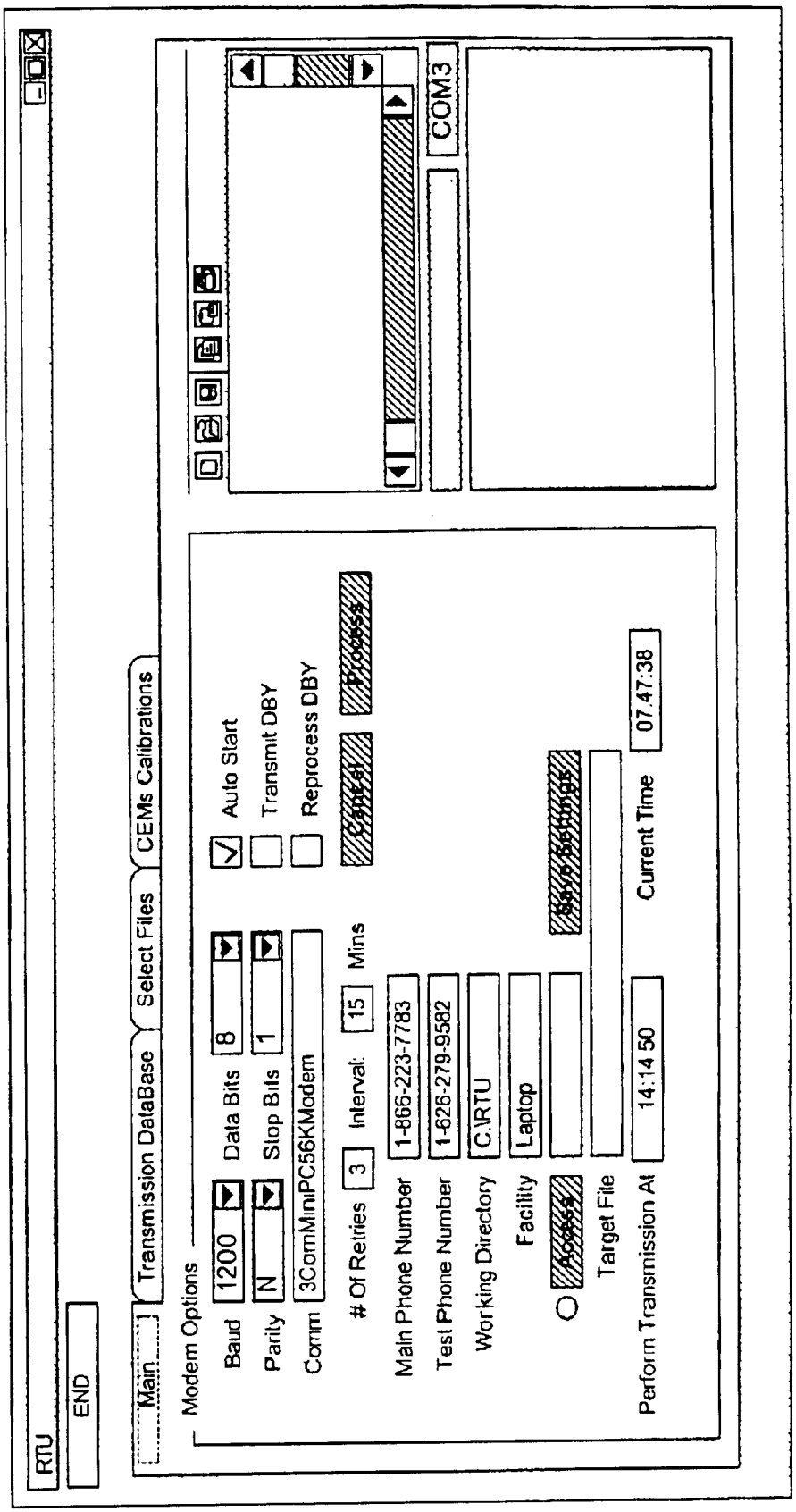
Figure 9:
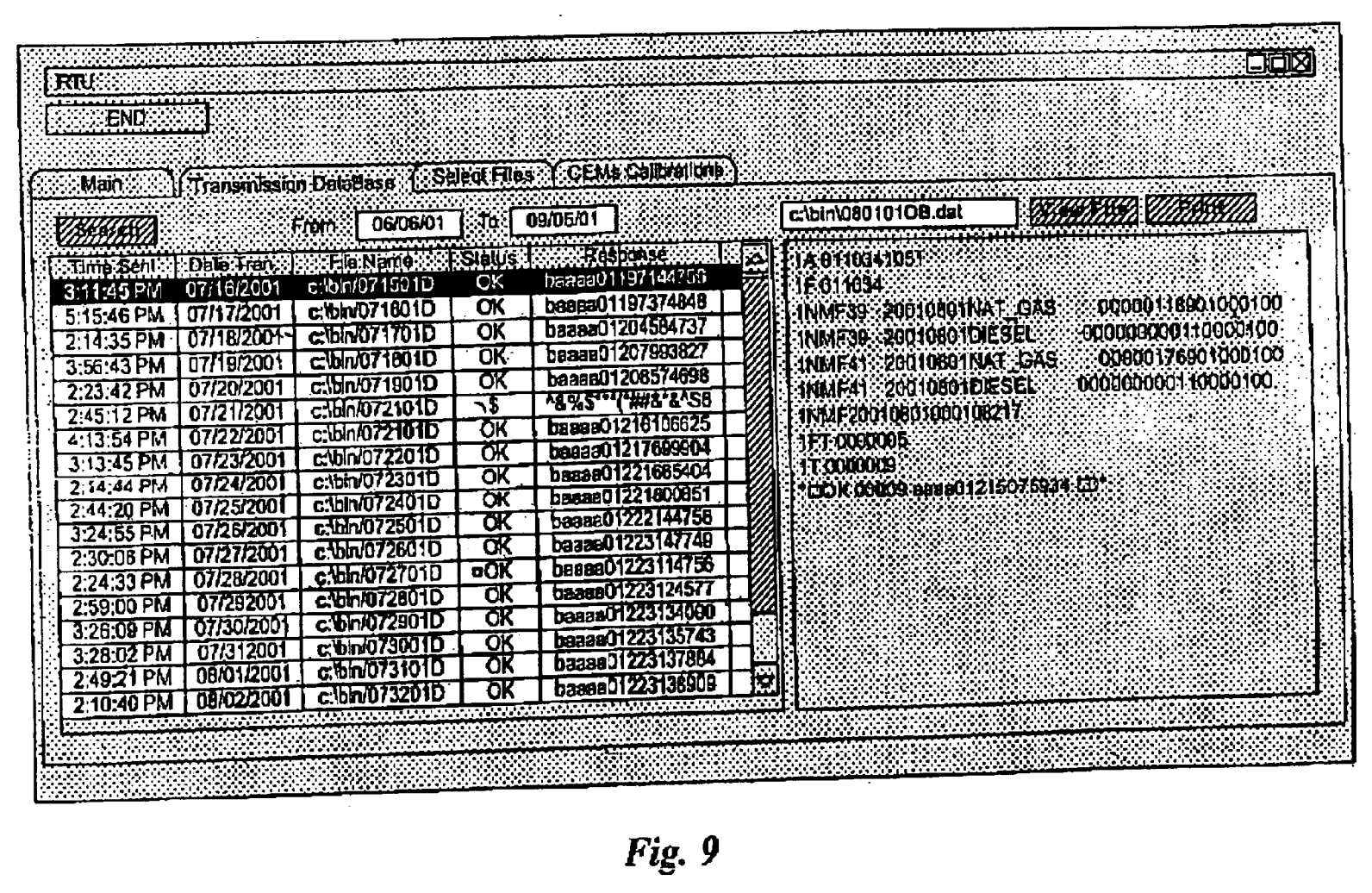
Figure 10A:
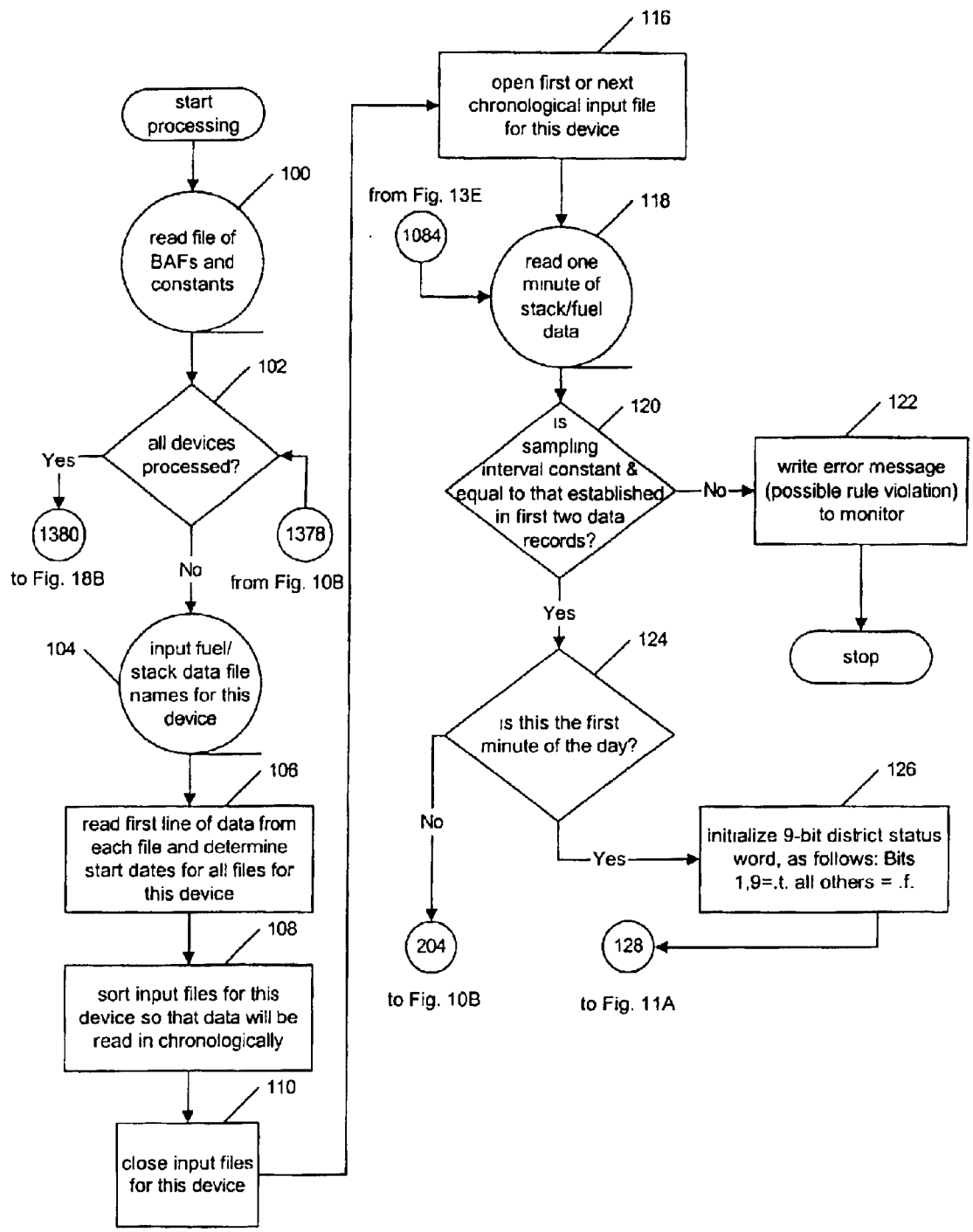
FIGS. 10A–18B are flow diagrams illustrating example processes implemented by the data acquisition system according to an embodiment of the present invention.
Figure 10B:
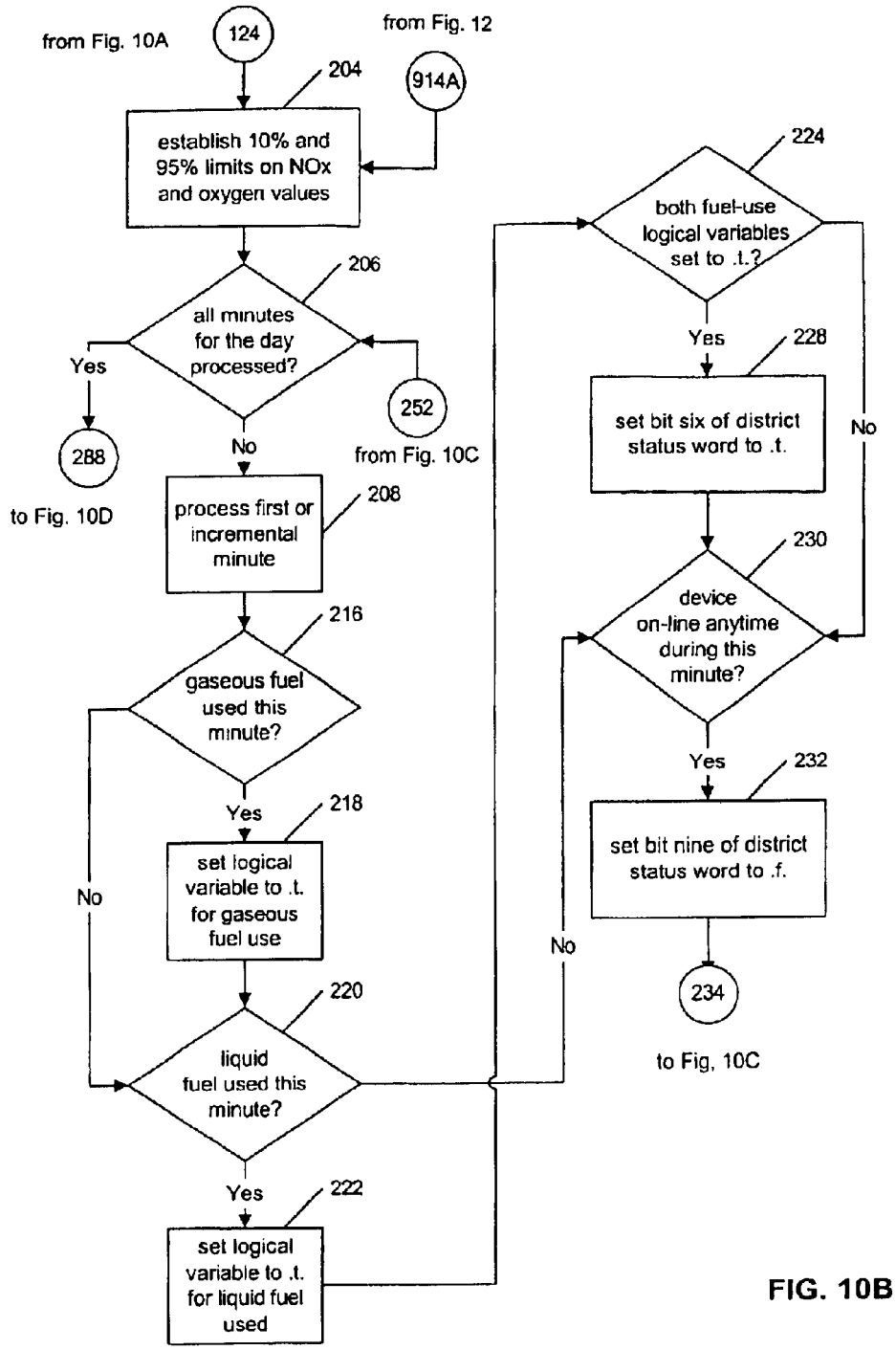
Figure 10C:
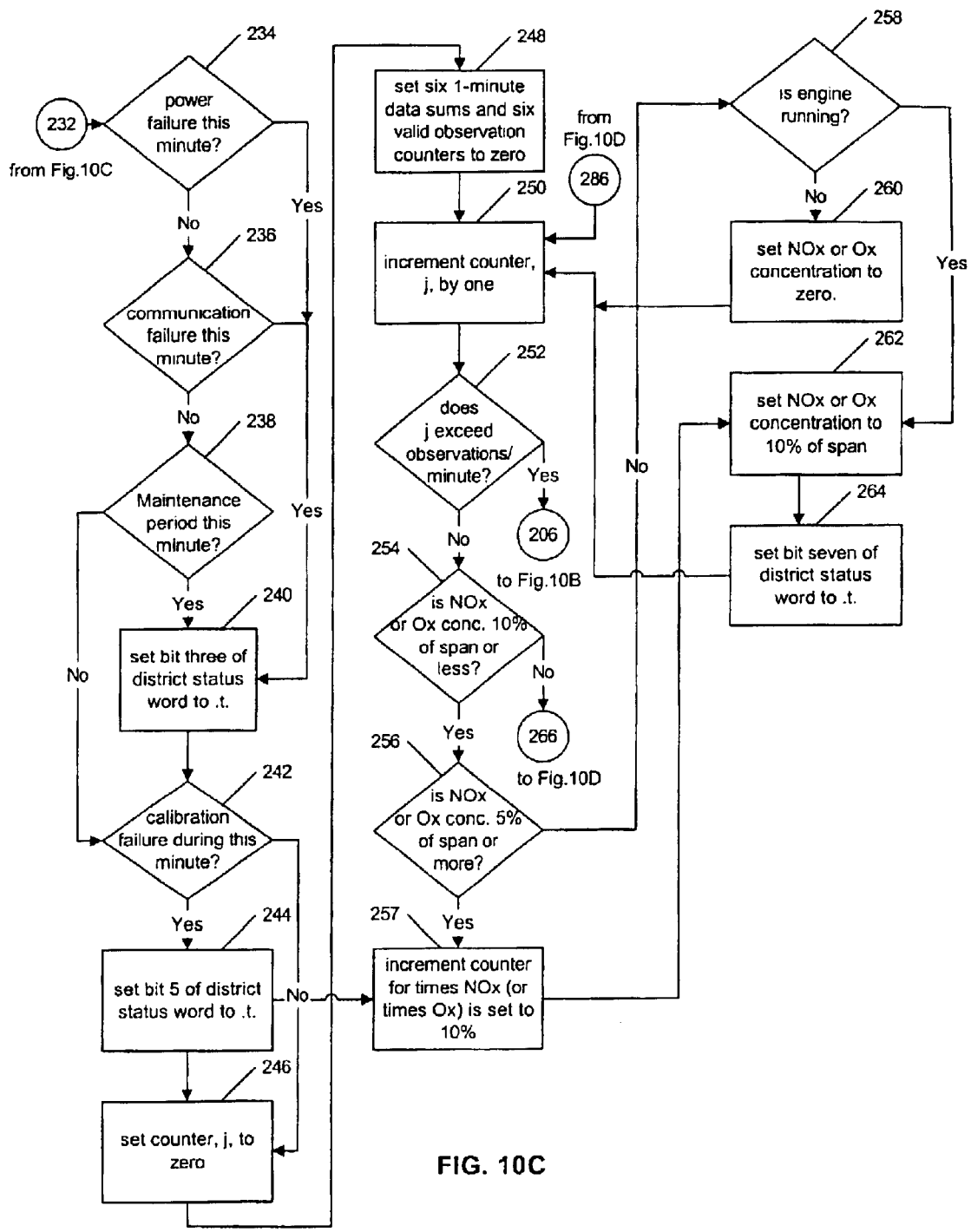
Figure 10D:
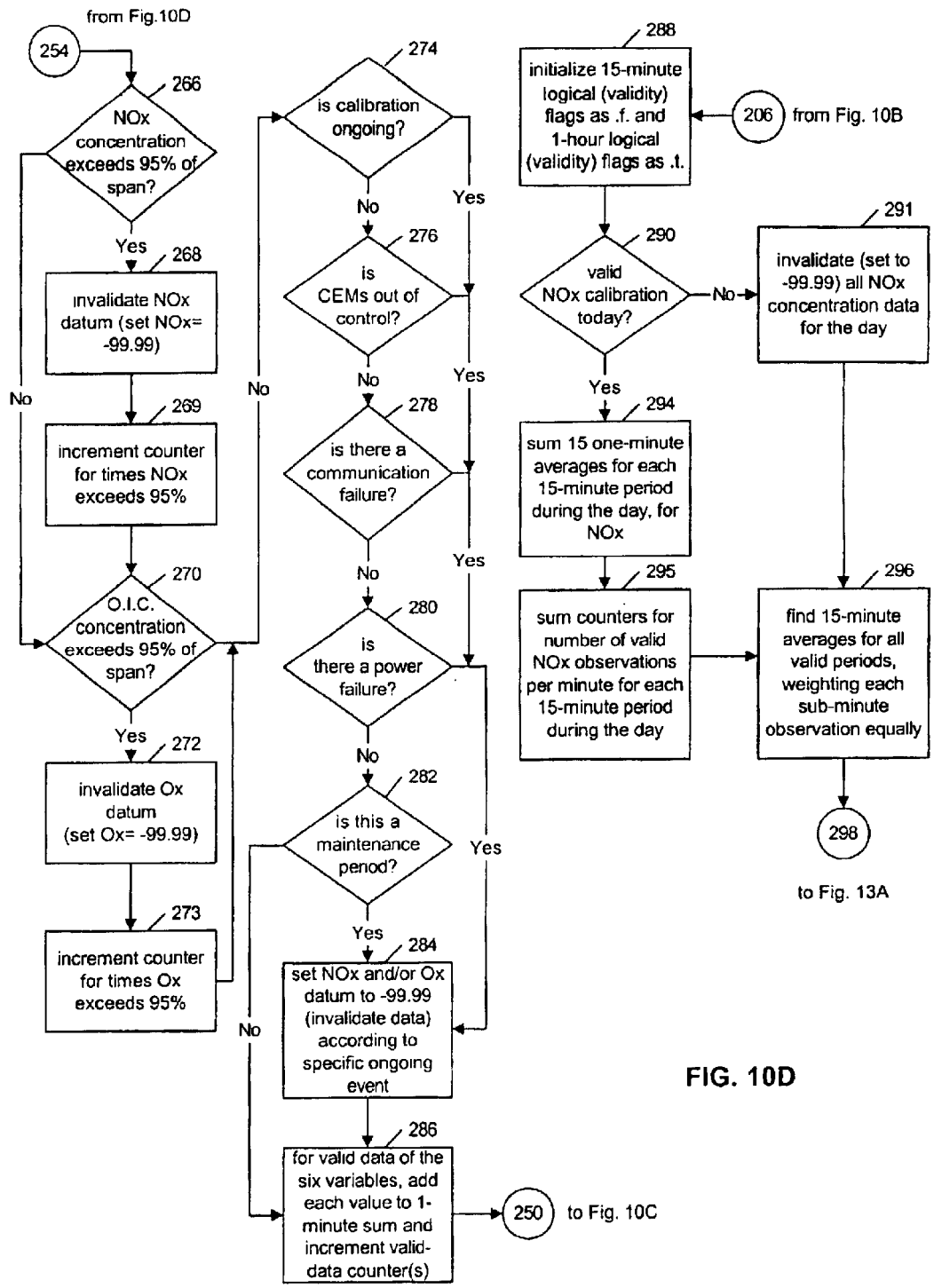
Figure 11A:
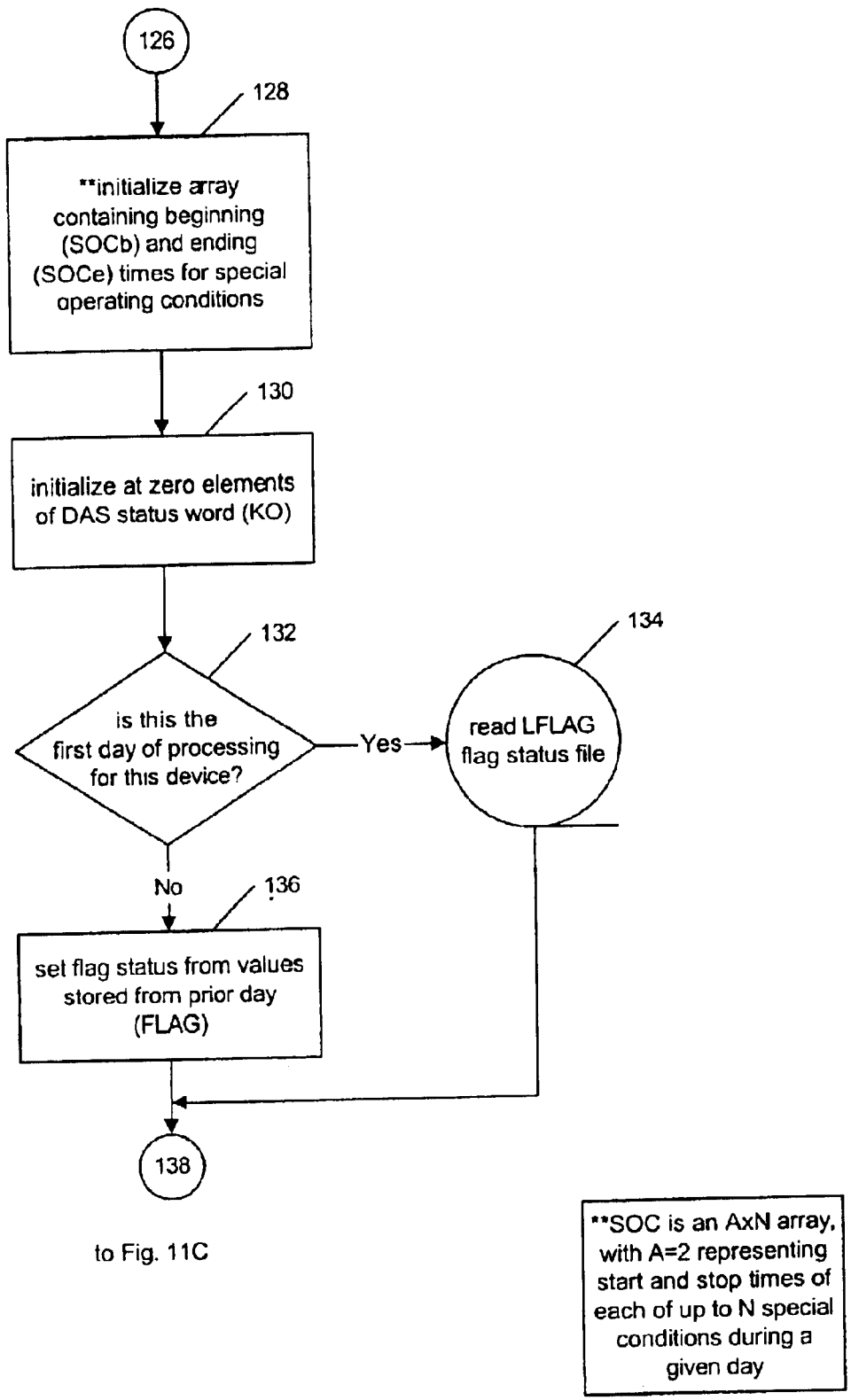
Figure 11B:
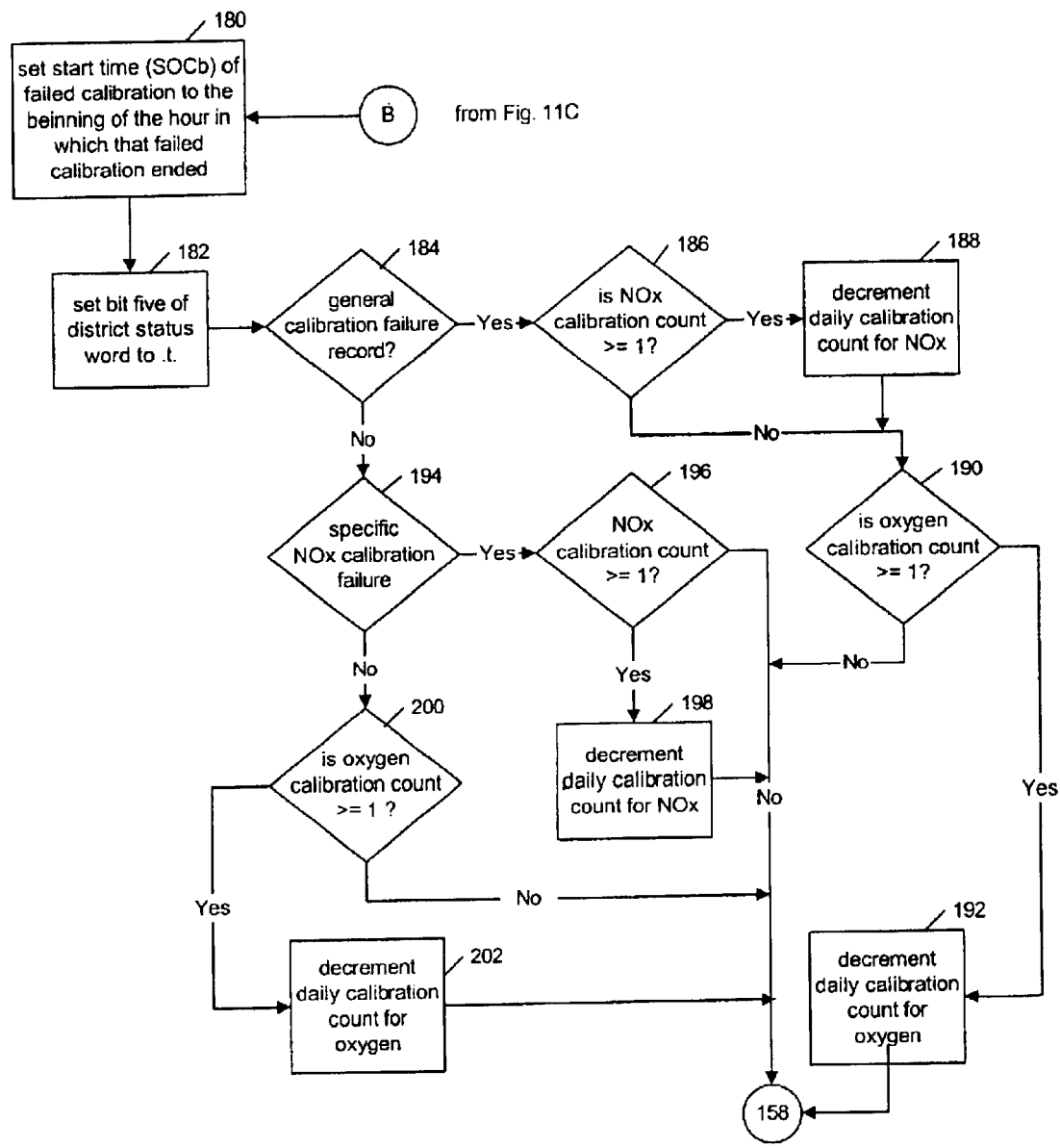
Figure 11C:
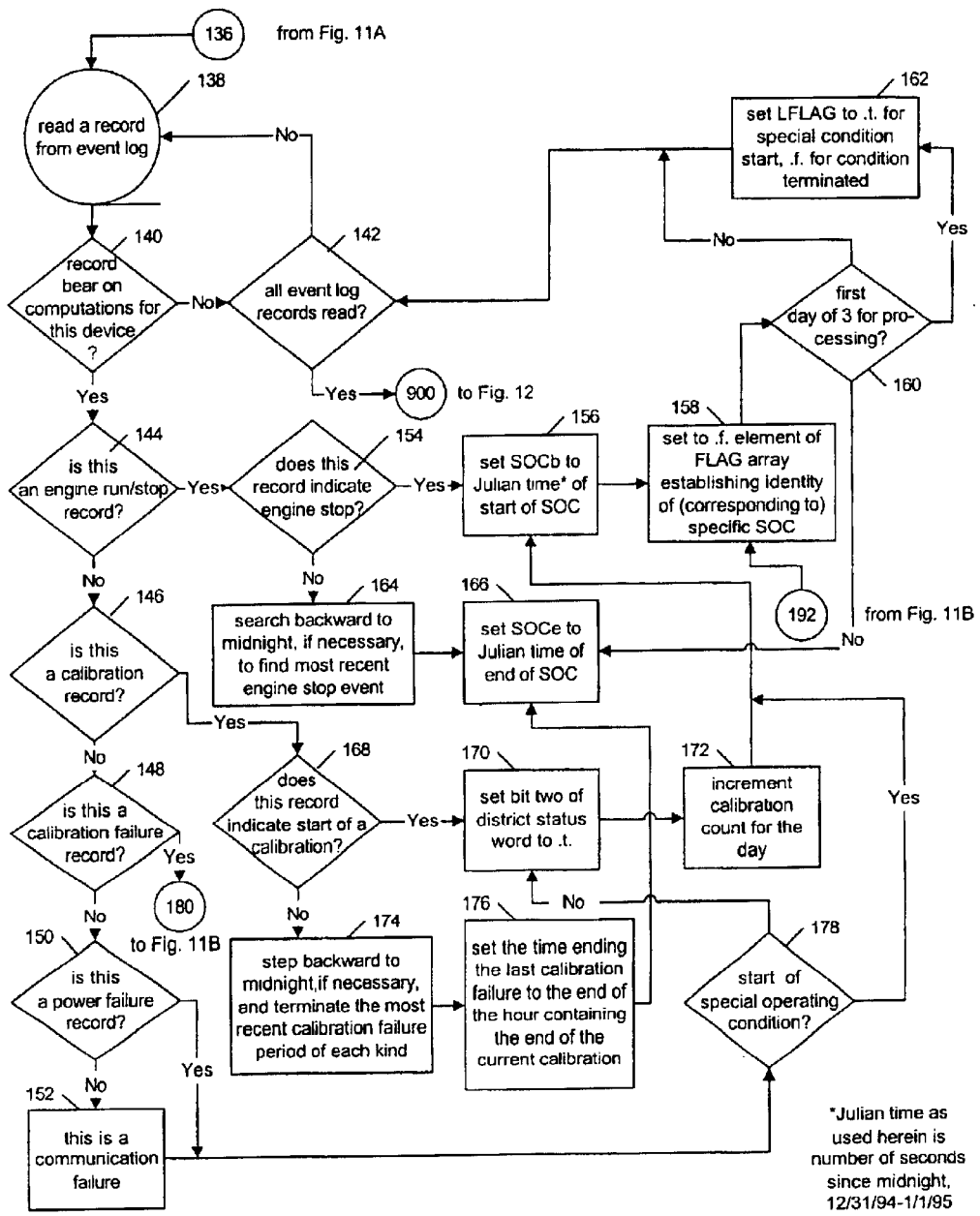
Figure 12:
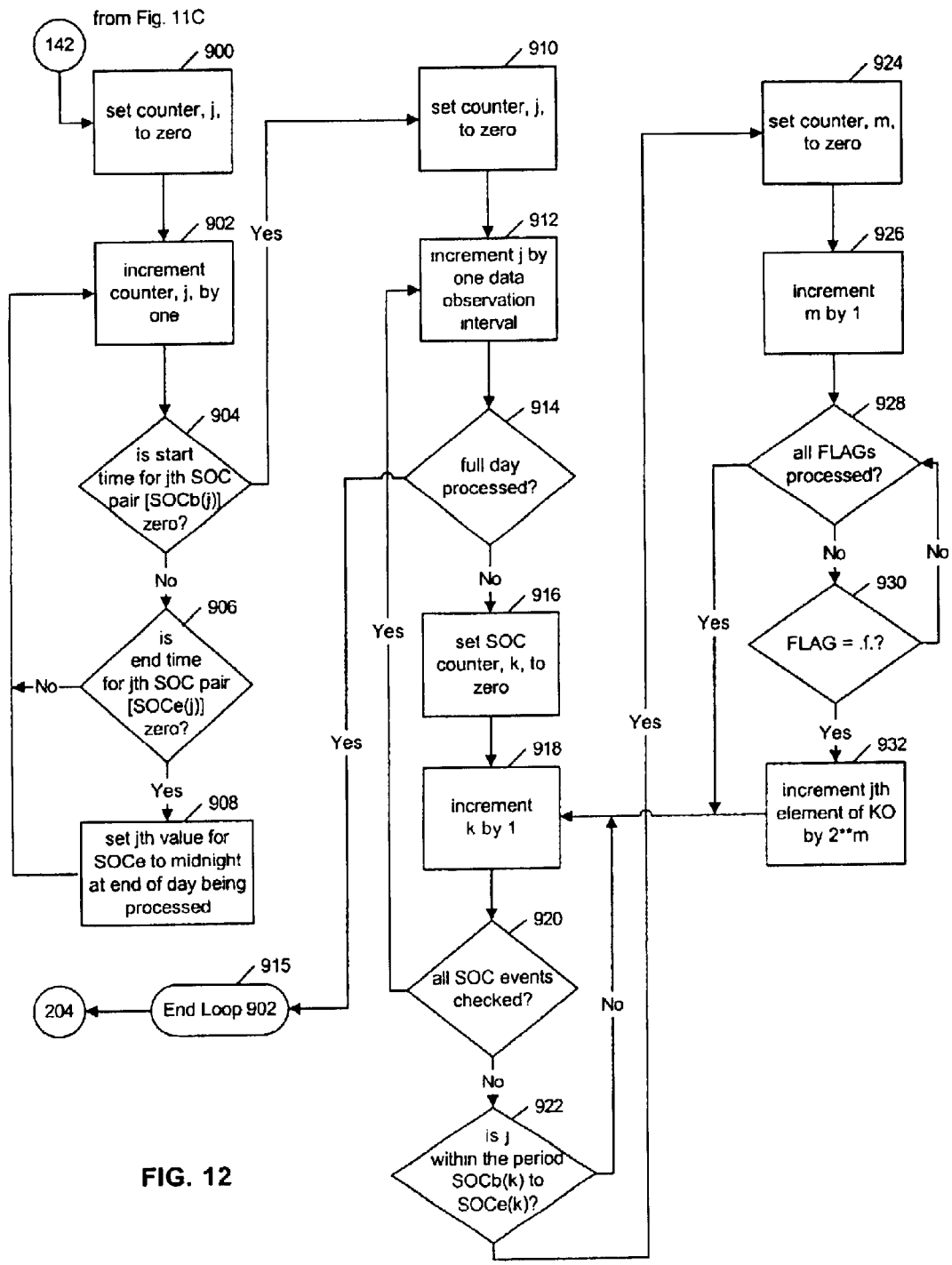
Figure 13A:
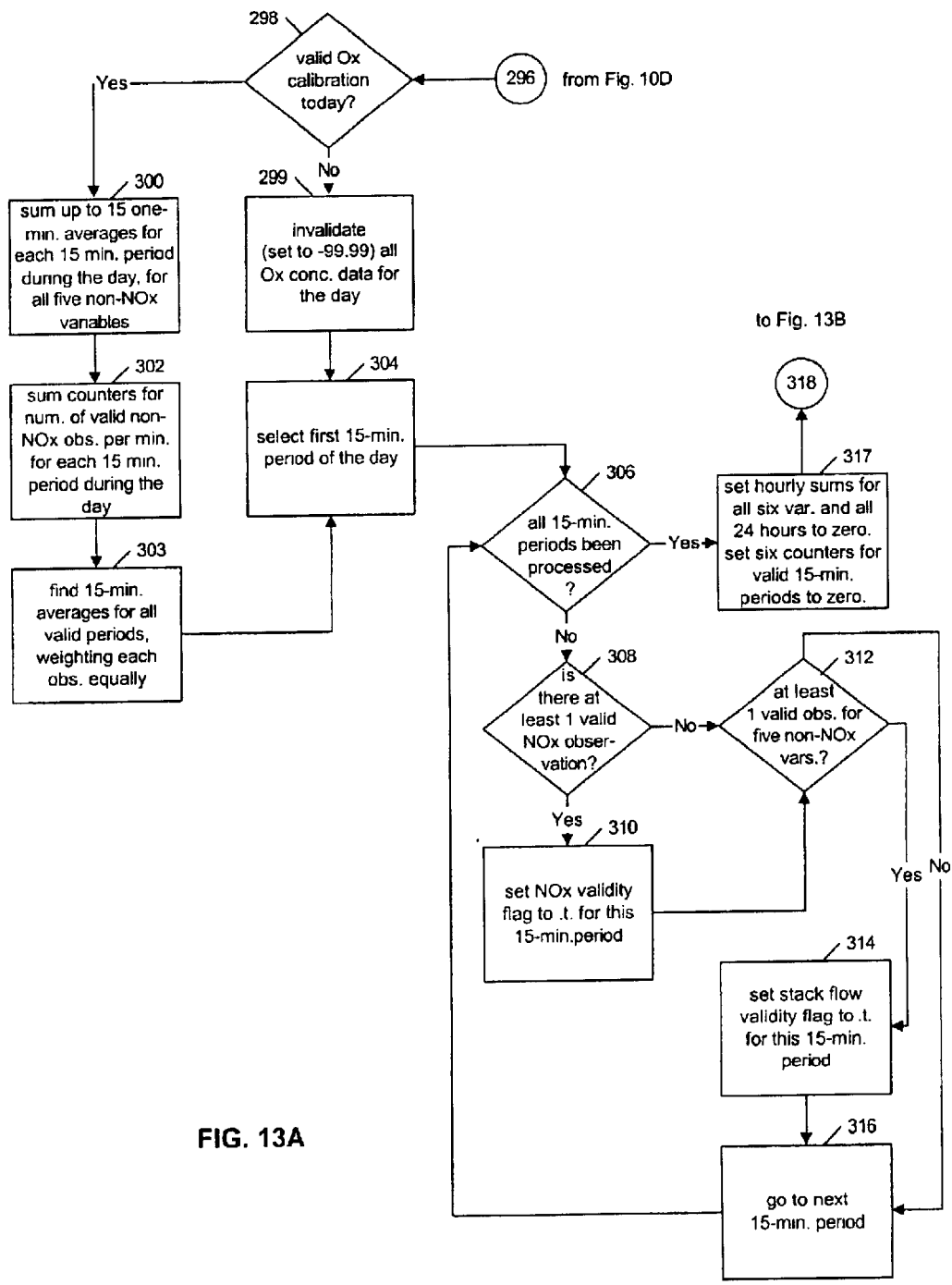
Figure 13B:
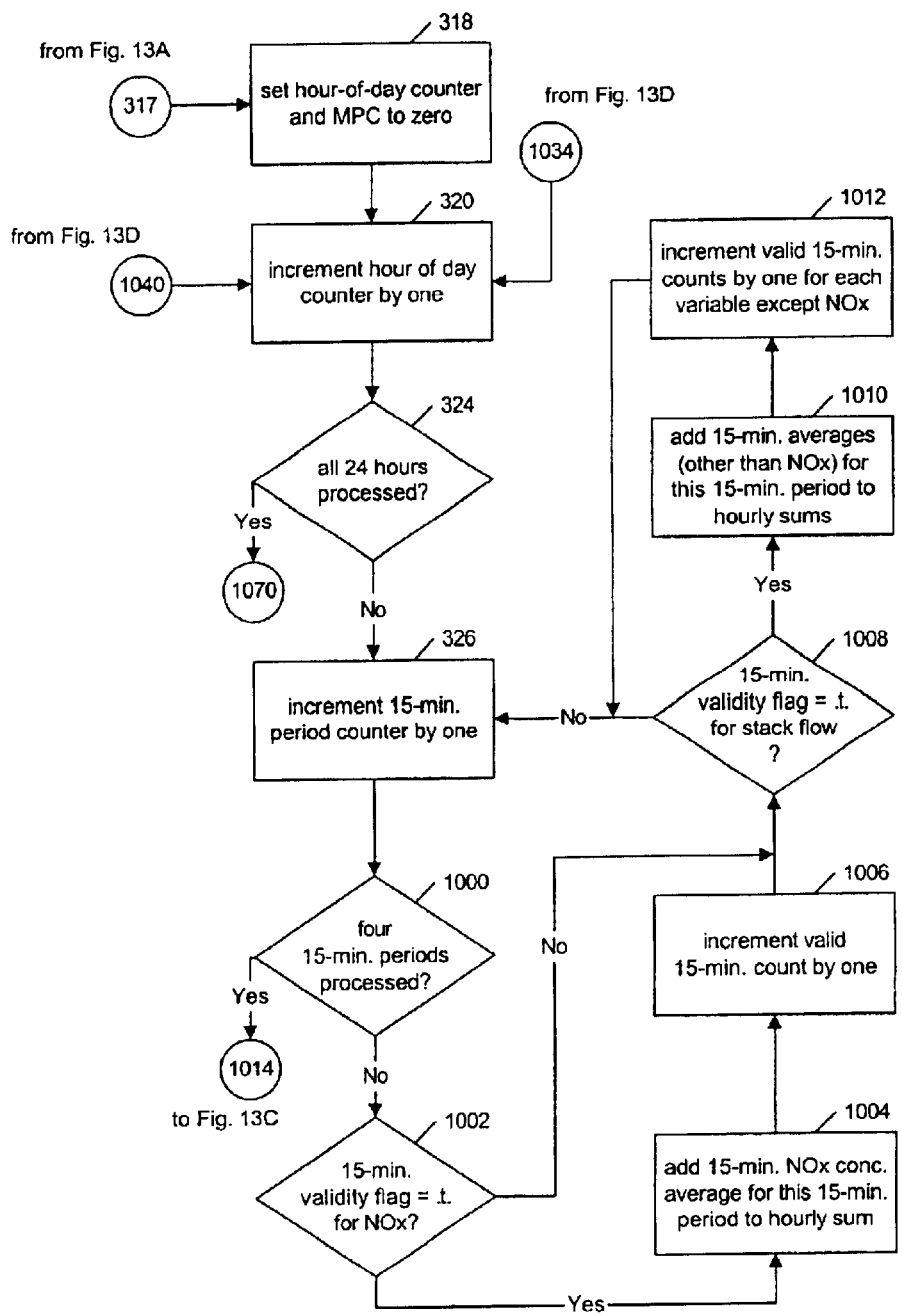
Figure 13C:
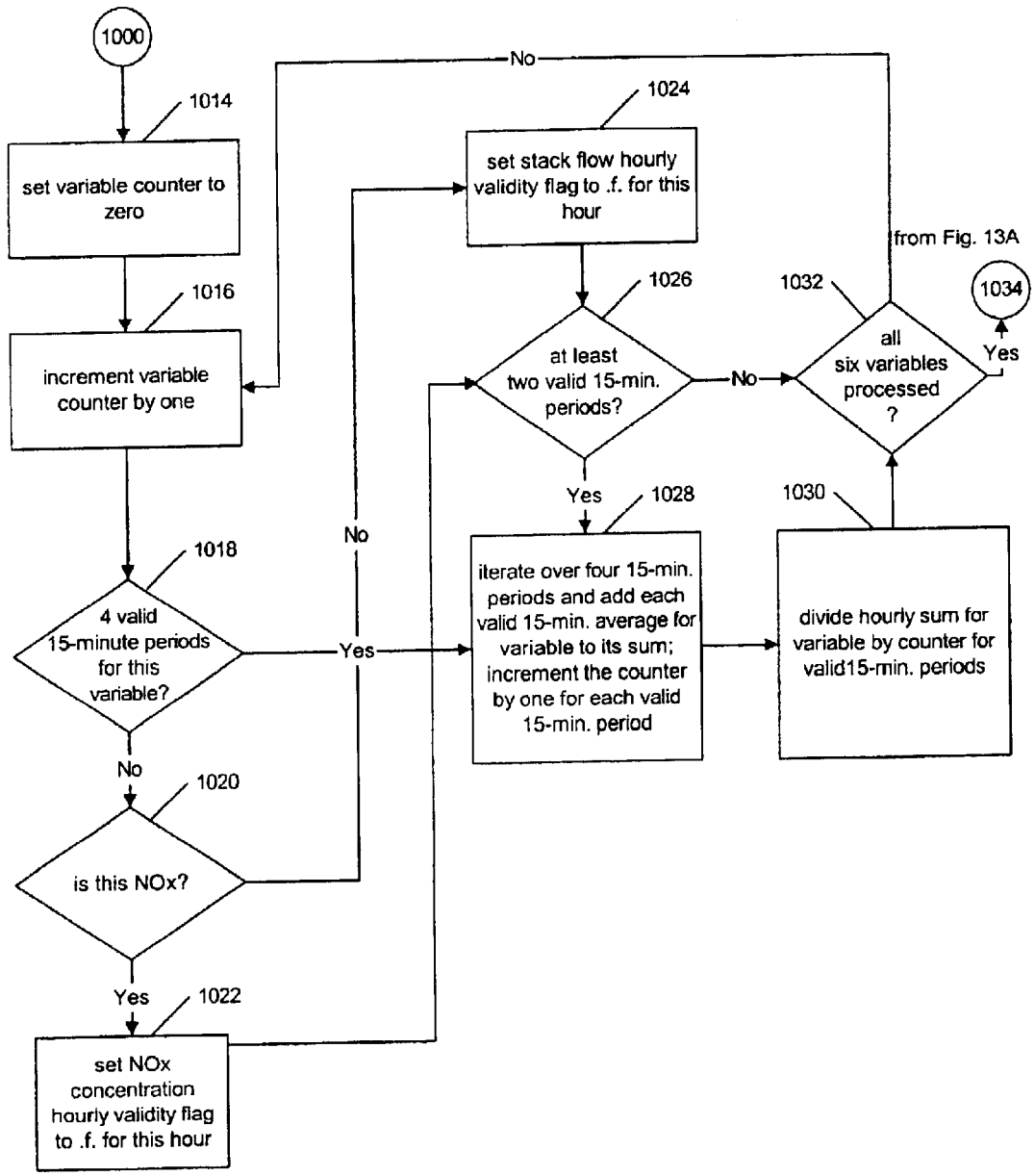
Figure 13D:
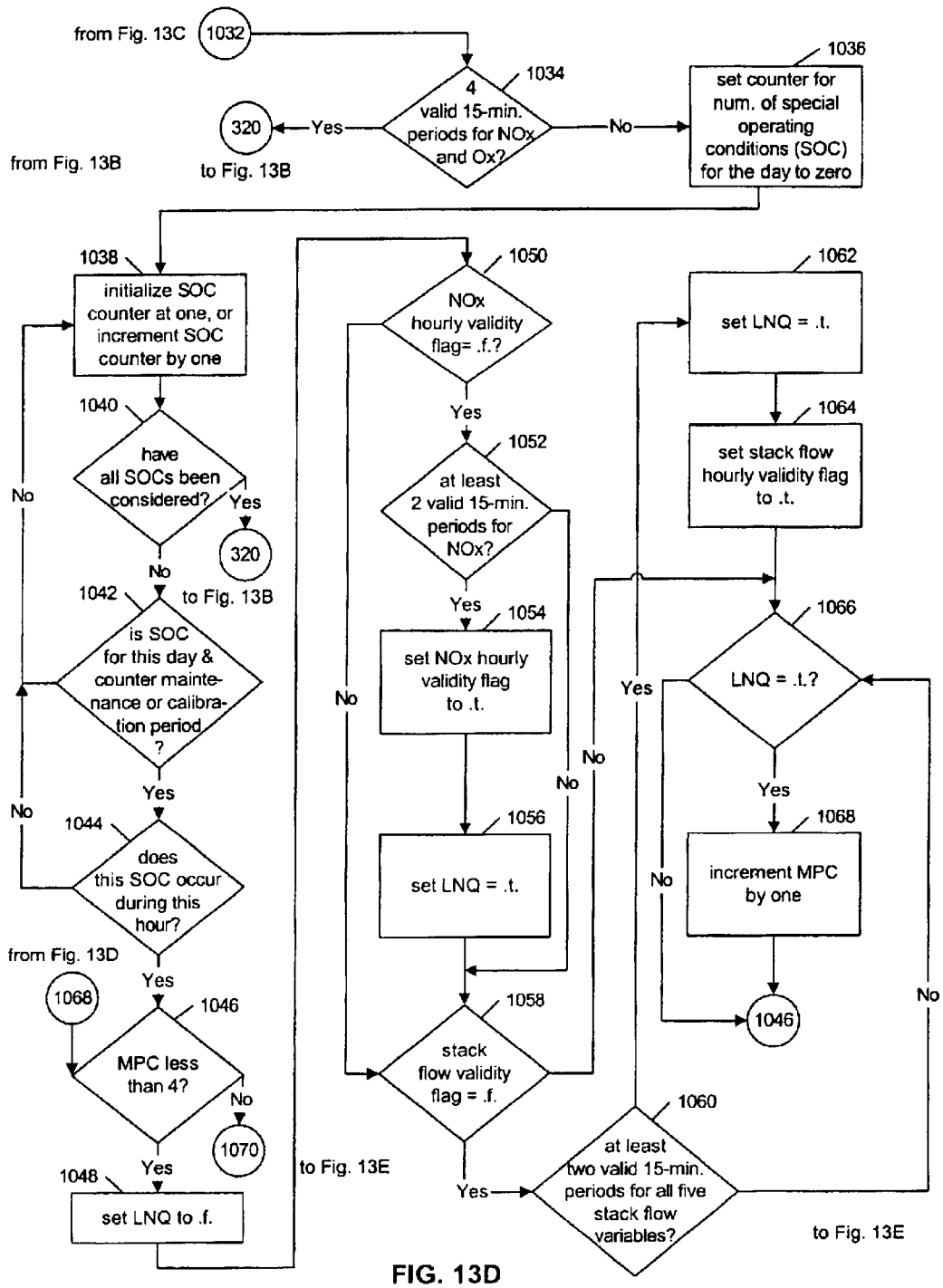
Figure 13E:
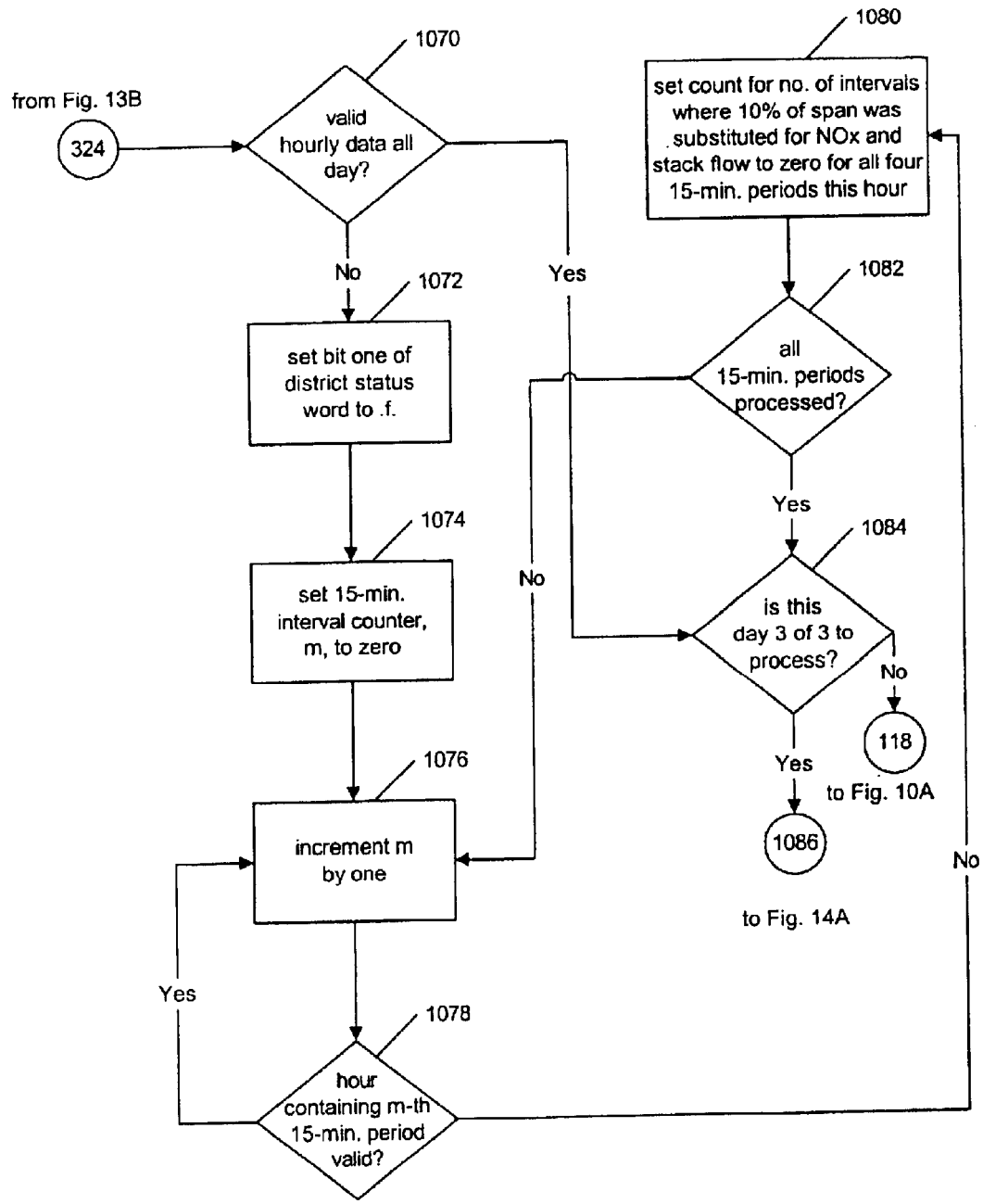
Figure 14A:
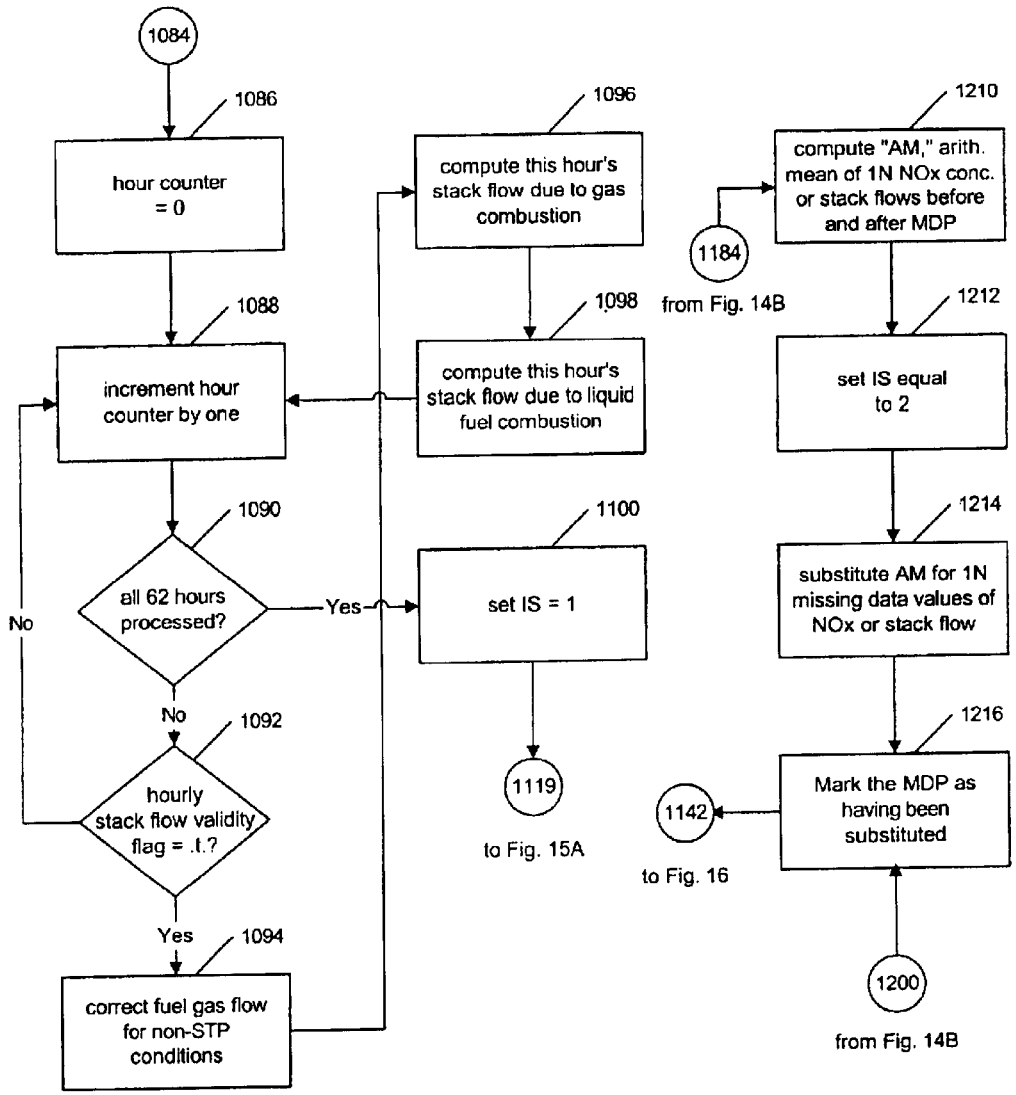
Figure 14B:
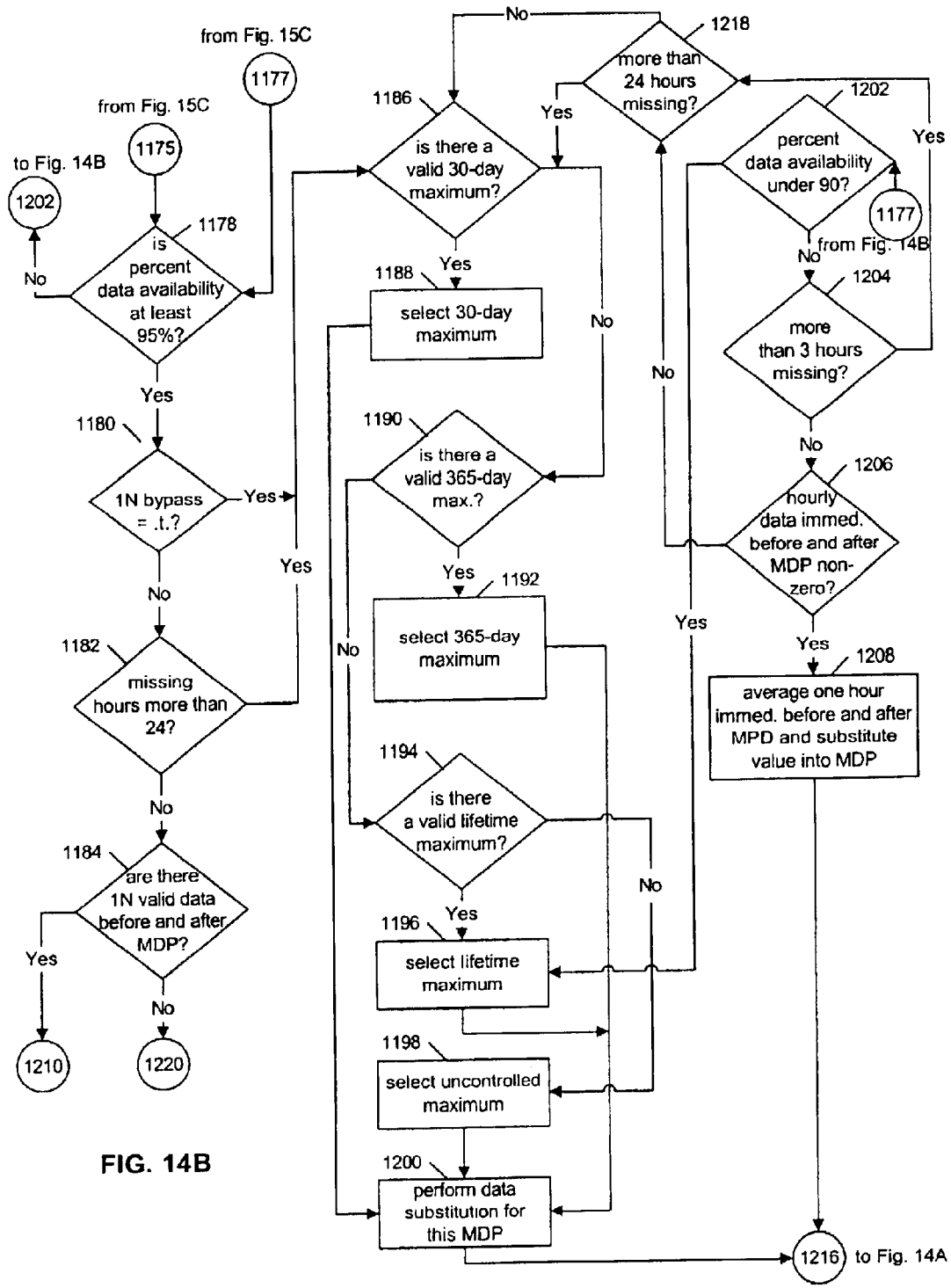
Figure 15A:
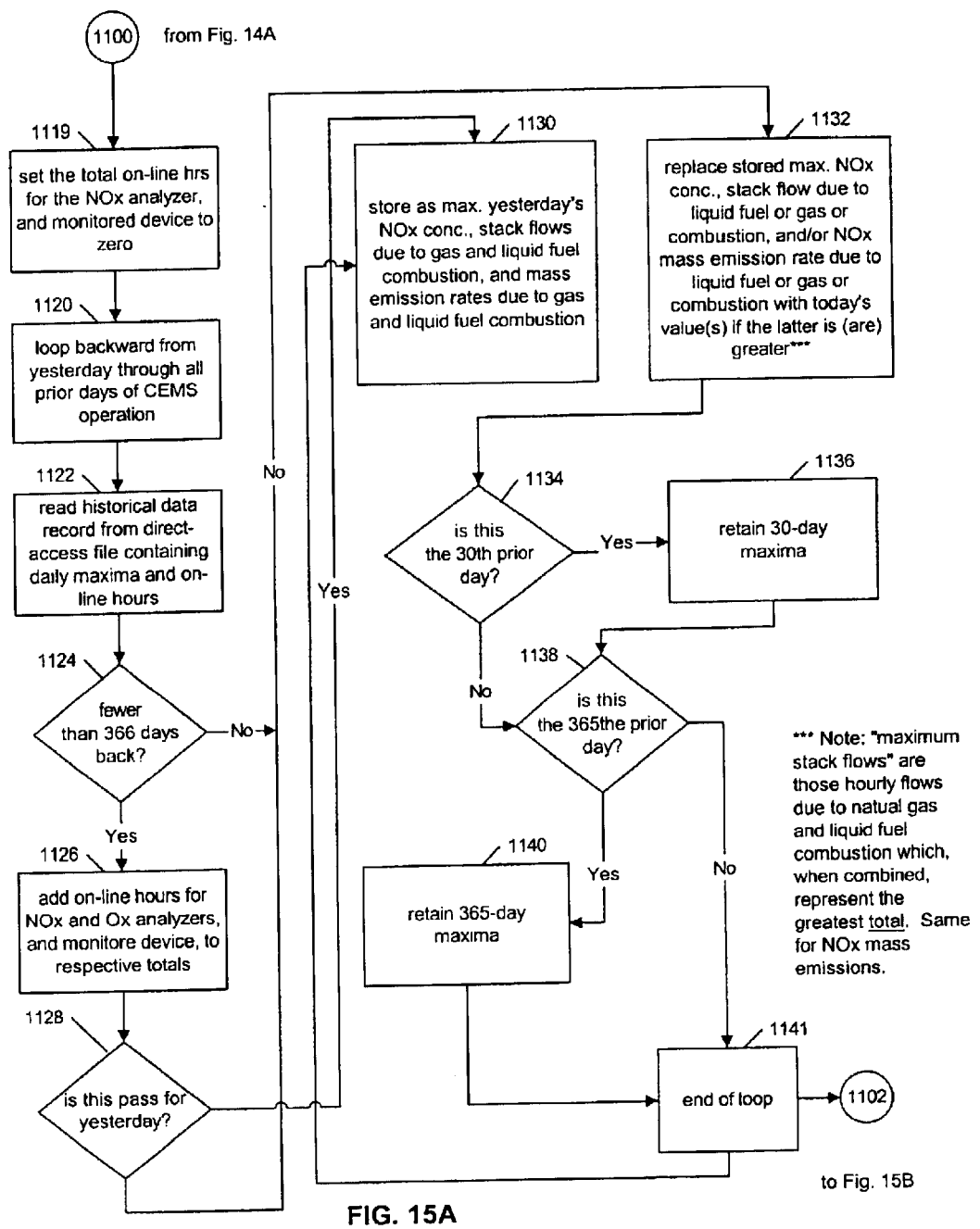
Figure 15B:
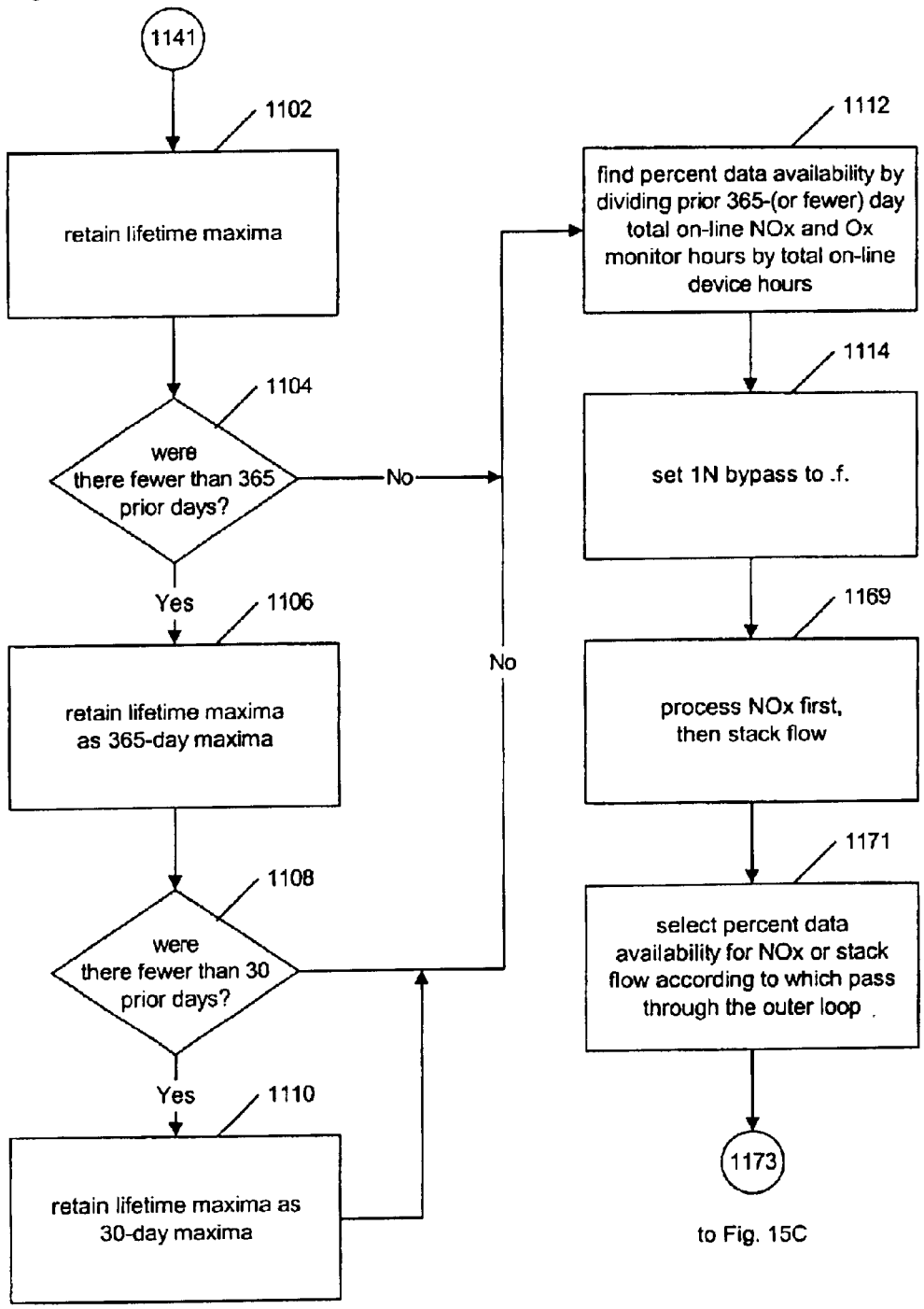
Figure 15C:
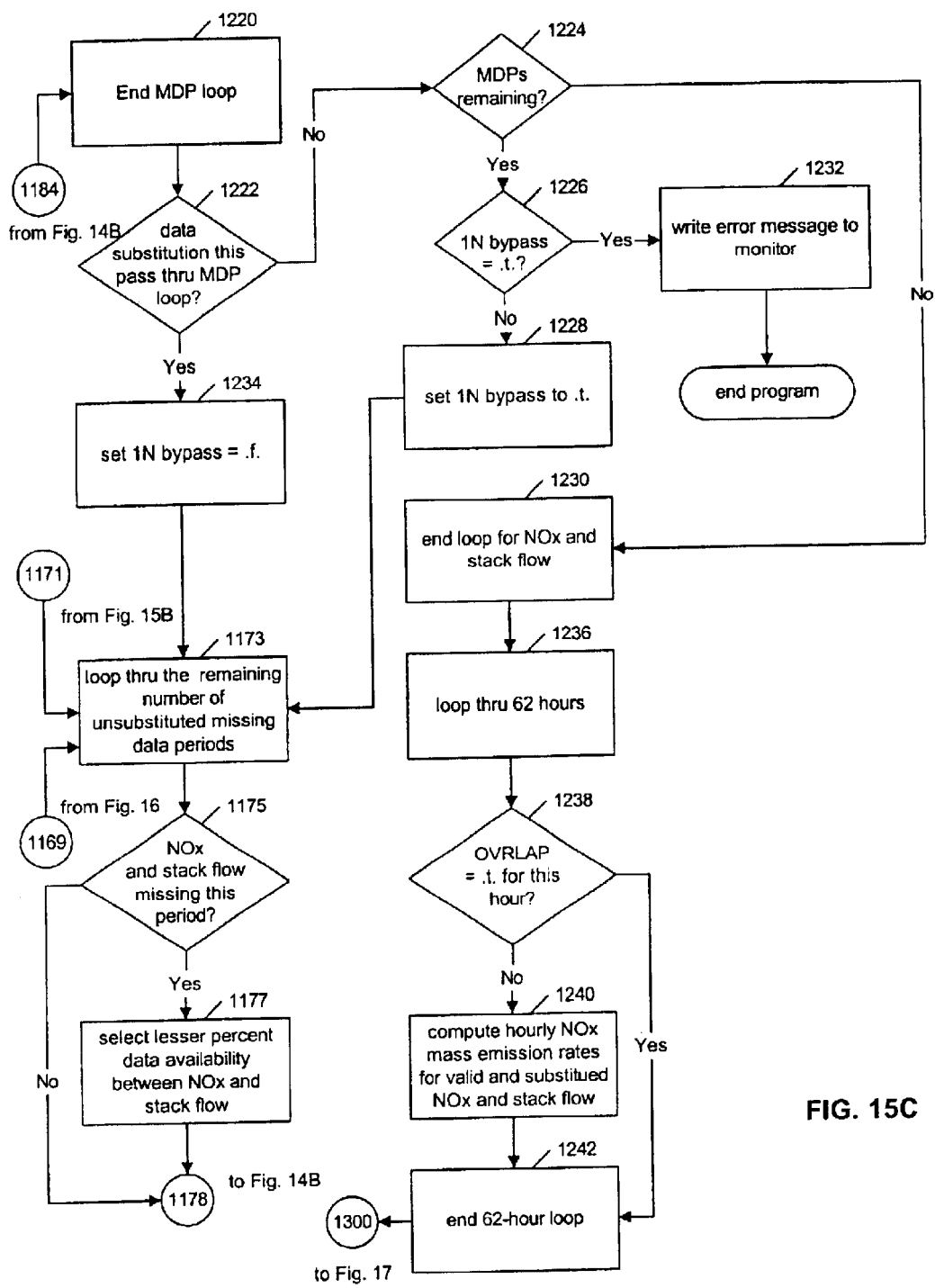
Figure 16:
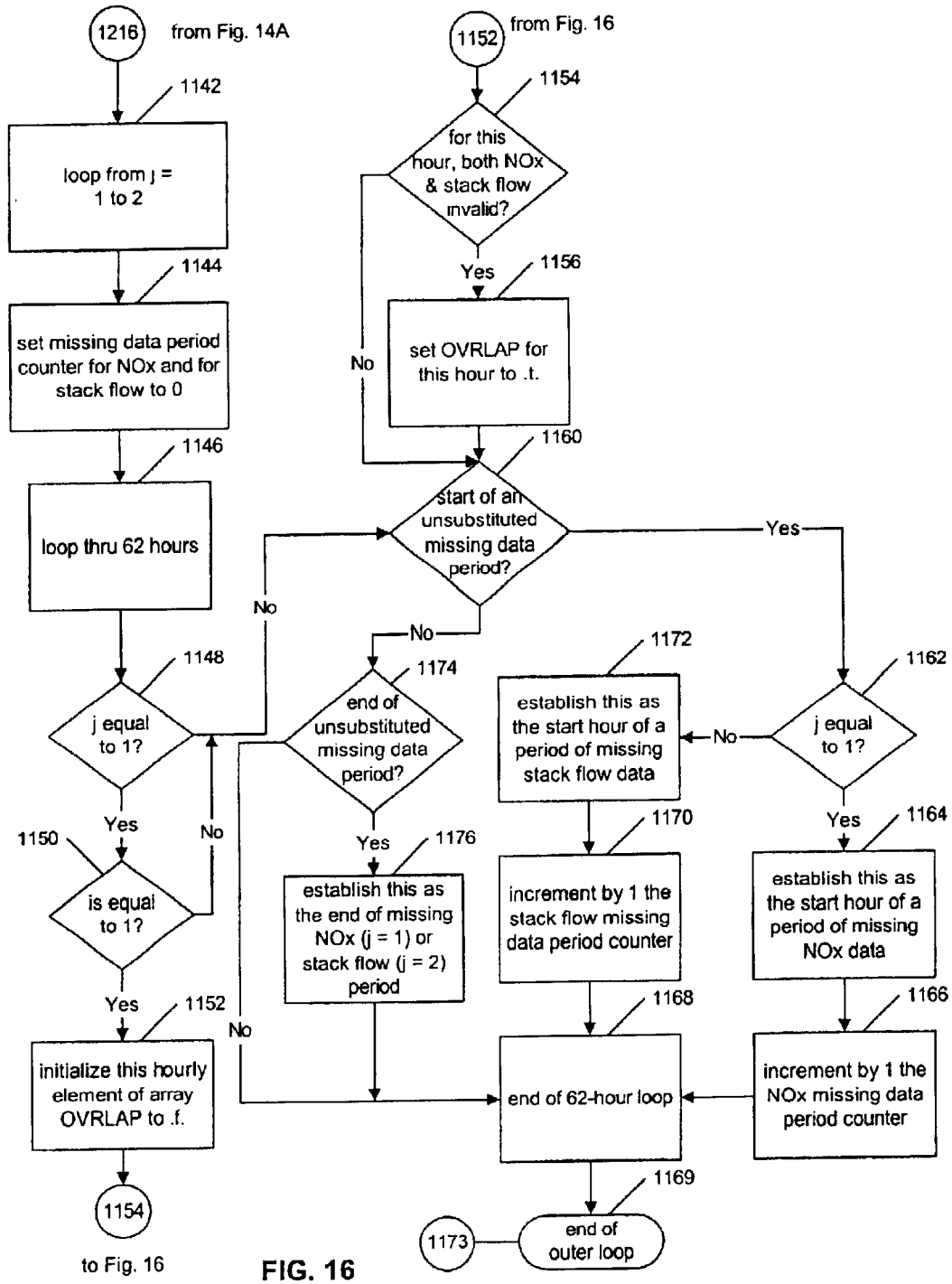
Figure 17:
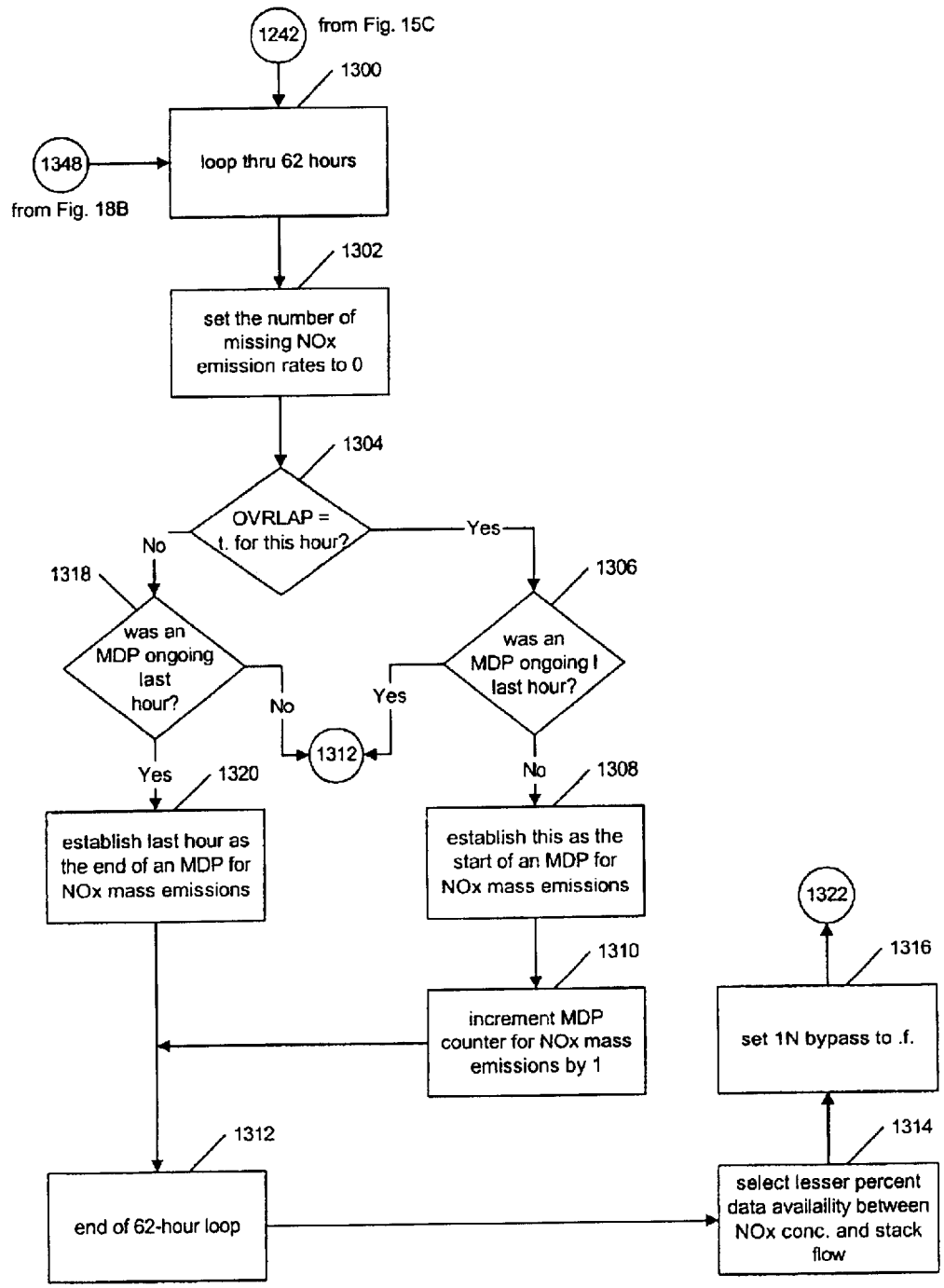
Figure 18A:
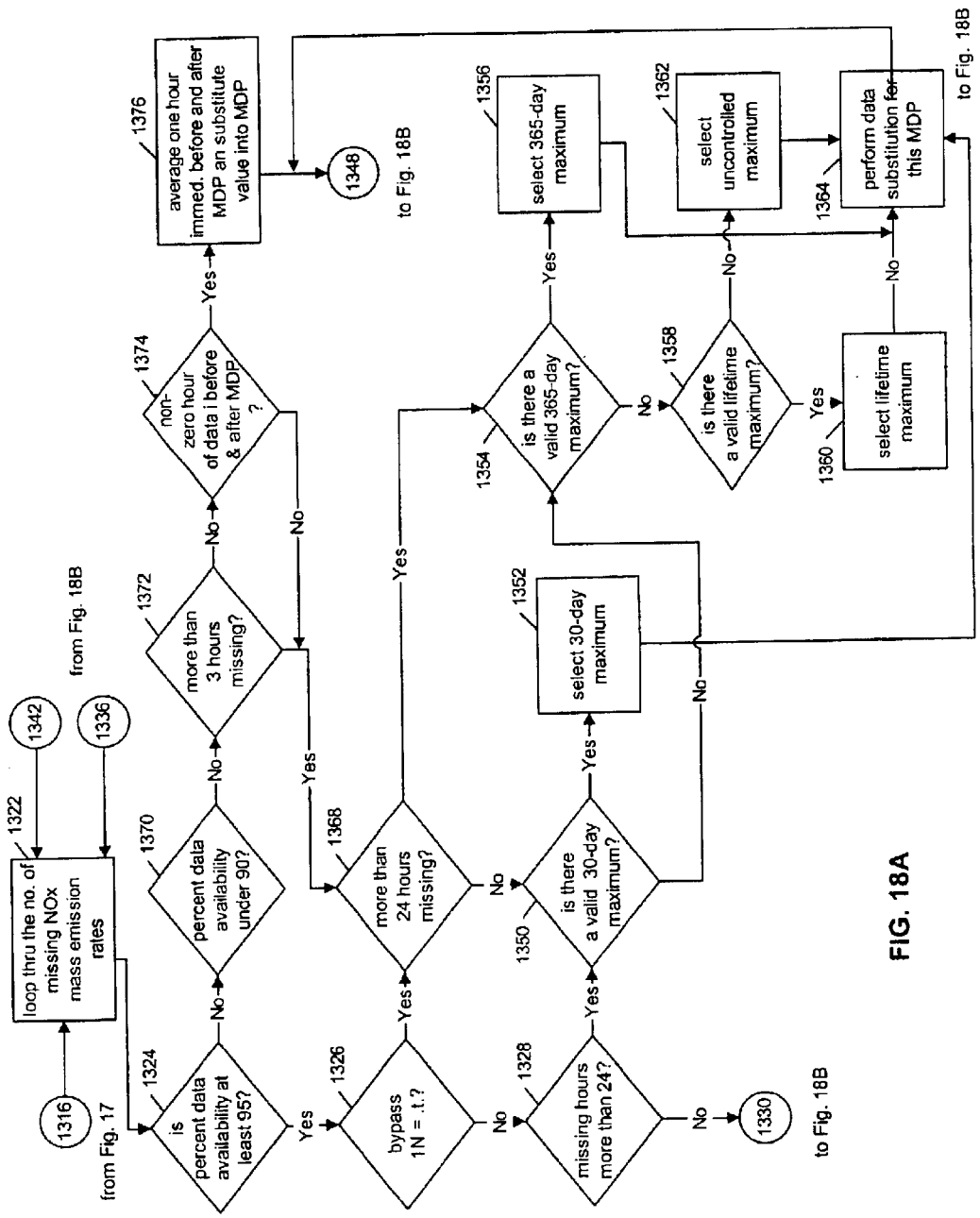
Figure 18B:
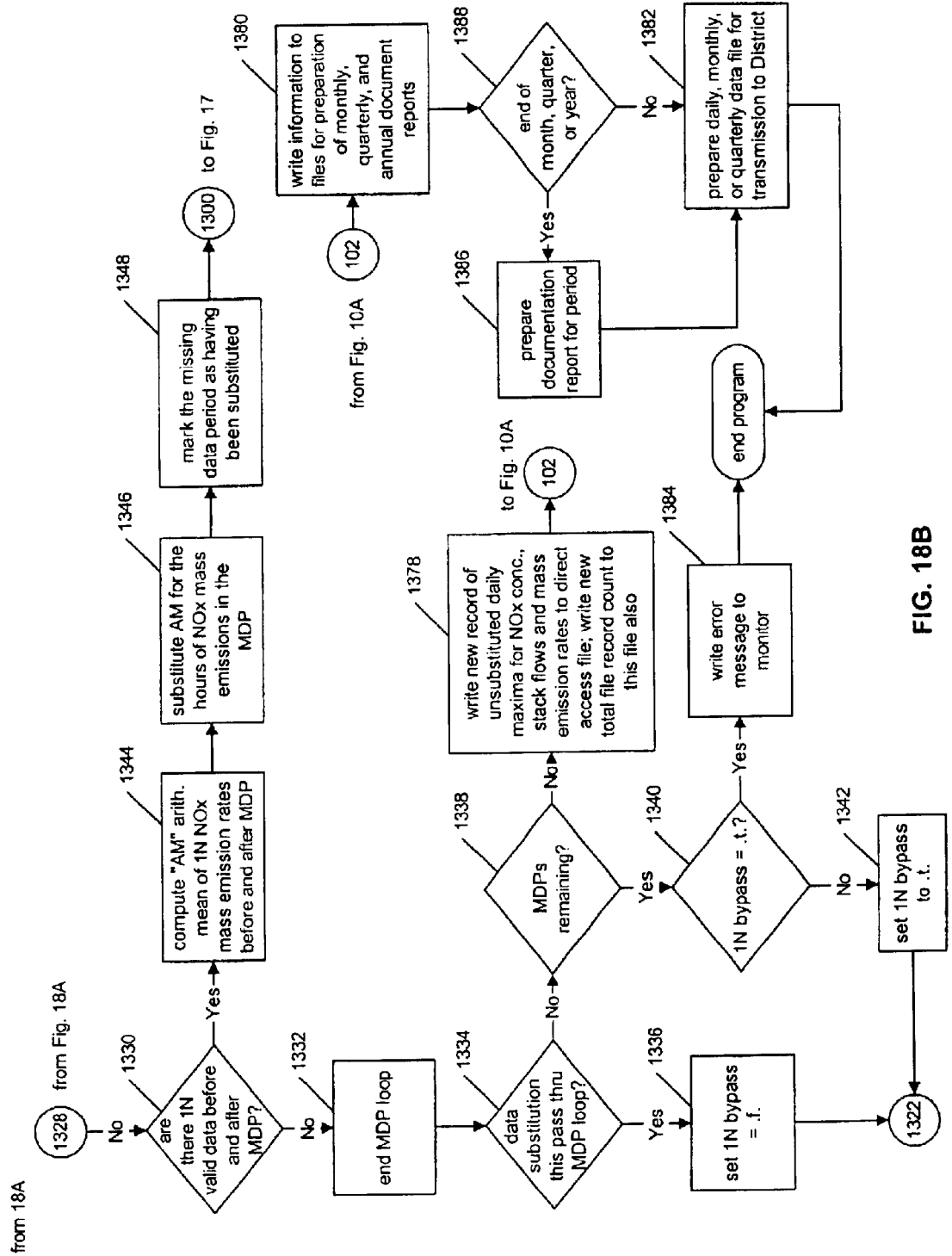

FIGS. 7–9 are screen shots of the RTU module's 28 transmission screens and file viewer.

DAS Method Steps Performed

With reference to FIGS. 10–18, a detailed flow diagram illustrating the steps performed by the data acquisition system is shown. Bias adjustment factor data and certain constants are read into the system, step 100. These data may be read or input from a file, and include information resulting from tests required by air quality management district (AQMD) regulations.

The user can choose stack data file names to process for each device if the data acquisition system was executed manually by a user, step 104. Otherwise, default stack data file names for each device are used. Thus, the system has the ability to process historical stack data if desired. In steps 106 and 108, the stack data files are sorted by date as read from the first line of data in each stack data file, step 108 and closed, step 110.

For each device, the system begins processing the stack data files in chronological order, step 116. One minute's worth of data is read from the data file, step 118. The system checks to see if the sampling interval is constant, step 120. If not, then an error is displayed to the user, step 122, and the system is halted. Otherwise, if the first minute of the day for the current stack data file is being processed, then a 9-bit district status word is initialized, step 126, where the required district status word values are to be stored during processing before transmission. Processing moves to step 128, where an array is initialized, called SOC array herein, for storing special operating condition information.

A DAS status word array is initialized by setting its elements to zero, step 130. If the first day of the last three days is being processed, step 132, then an LFLAG array is read from a status file, step 134, which indicates the status of the day before the first of three days being processed. Otherwise, the flag status from values stored the prior day is set in a FLAG array, step 136. The LFLAG array contains 10 elements representing 10 different special operating conditions which bear upon monitoring data processing or validity, i.e., device stopped, calibration ongoing, general calibration failure, power failure, communication failure, NOx analyzer span calibration failure, NOx analyzer zero calibration failure, oxygen analyzer span calibration failure, and oxygen zero calibration failure. If all conditions are normal, then each element is set to "true." When the special operating condition begins, the corresponding element is set to "false." LFLAG is thus used to store the status of the special operating conditions so that when the DAS 26 finishes processing a group of three sequential days, LFLAG contains the special operating condition statuses at the end of the first of those three days. Each day, the DAS 26 processes a group of three days, moving forward only one day per day, so that on any given day, the first and second day to be processed are the same as the second and third days processed the day before. LFLAG thus provides the status of the special operating conditions at the beginning of the first day of processing whenever the DAS is invoked.

The FLAG array also consists of 10 elements, and their meanings correspond to those of LFLAG. The difference is that the FLAG array is used to track the statuses of the special operating conditions at all times during the three days the DAS 26 is processing. Accordingly, LFLAG is updated only at the end of processing of the first day of data. A FLAG record is created/changed whenever a special operating condition begins or ends during the three days being processed. Accordingly, at the end of the first day, LFLAG will always be identical to information contained in the FLAG array at that point in time.

The system opens the event log for the current device being processed, step 138. Each record in the event log is then processed. The system checks to see if the record being processed relates to computations for the device, step 140. If not, then the system checks for whether the end of the event log has been reached, step 142. If not, then the next record is read from the event log file at step 138.

The system checks for whether the event log record is an device run/stop record, step 144, calibration record, step 146, calibration failure record, step 148, power failure record, step 150, or a communication failure record, step 152.

If the event log record is a device run/stop record, then the system checks to see whether the record is a device stop record, step 154. If so, then a record is added to the SOC array (created in step 128), including a time stamp, or Julian time, of this special operating condition, steps 156–158. A Julian time is similar to a Julian date, and herein represents the offset in seconds from the beginning of the day on Jan. 1, 1995, which is the reference time from which all times are computed for DAS data processing purposes. The record also includes the values of the 10-element FLAG array, nine of which are set to true and one, corresponding in location in the array to the type of special operating condition, is set to false, for each special operating condition that is initiated during the day. For device stop in the present embodiment, this is the first element. A third type of data is included in the record: the beginning and ending times for the special operating condition, i.e., device stop. That is, the beginning time is when the device was stopped. The ending time is the first time the device is started following the device stop.

The system next checks for whether the first day is being processed of the three day period currently being analyzed, step 160. If so, then element one of LFLAG is also set to false to represent device stop, 162. Processing moves back to step 142 and then 138 for processing the next record.

If the result of step 154 was no, then the event is an device start, and the system searches backward in the SOC array to find the most recent device stop event, step 164. Once found, the SOC array record field representing the end time is updated to reflect the time when the device was restarted, step 166. Processing then moves back to step 160.

If the currently processed event log record is a calibration record, step 146, the system checks to see if the event log record indicates the start of a calibration, step 168. If so, then the calibration bit is set in the district status word, step 170. A daily calibration count is incremented, step 172. Processing moves back to step 156.

If the condition in step 168 resulted in no, then the system steps backward to find the most recent failed calibration entry into the SOC array for both NOx and Ox analyzers (chemical analysis instruments within the CEMS), step 174. That most recent calibration entry is updated to reflect an ending time that is the end of the hour for the currently successful calibration, step 176. Processing moves back to step 166.

If the event log record currently being processed is a power failure record, step 150, then the system checks for whether the event indicted was the start of a power failure, step 178. If so, then processing moves to step 156. Otherwise, processing moves to step 166.

If the event log record was a calibration failure record, then processing moves to step 180, where the start time of the failed calibration is set in an SOC array record. The calibration failure bit is set in the district status word, step 182. The system checks for whether the failure was a general calibration failure, step 184. If it was, then a NOx daily calibration count is decremented if non-zero, steps 186–188, as well as an oxygen daily calibration count, steps 190–192. Processing moves to step 156. District rules require that for a day's data to be valid, the CEMS must be calibrated successfully at least once. It doesn't matter when the calibration occurs, but there must be at least one. It is not unusual for the facility to do multiple calibrations on a given day for whatever reason they may have. Several, one, or none of those might be successful. The counter is incremented each time there is a successful calibration (the event log records each cover only one discrete event, like calibration start, or calibration end, or calibration failure) and decremented (but not below zero) each time there is a calibration failure. The reason for preventing negative counter is that there may be extra (spurious) calibration failure messages in the event log, and the assumption is that there cannot be more calibration failures than calibration attempts. If the counter is any number other than zero, then there must have been at least one successful calibration. If it is zero, then the entire day's data are invalid.

If the calibration failure was not a general failure, then if the failure was a NOx analyzer calibration failure, step 194, then the NOx calibration count is decremented if non-zero, steps 196–198 and processing moves to step 156.

If the calibration failure was not a general failure, then if the failure was an oxygen analyzer calibration failure, then the oxygen calibration count is decremented if non-zero, steps 200–202 and processing moves to step 156.

Finally, if the event log record is a communication failure record, then the system checks for whether the record indicates the start of a communication failure, step 178. If so, then processing moves to step 156, otherwise, processing moves back to step 166.

After all event log records have been processed, then the system proceeds to process stack records from the stack/fuel data file starting with step 204. The valid data limits are established in step 204 as read in step 100, for example, 10% and 95% of limits for NOx and oxygen. The system then proceeds to processing the stack data for all minutes of the day, step 206. The system increments a minute counter, step 208. The system checks the fuel input data to see whether gaseous fuel was used, step 216. If so, then the logical variable for gaseous fuel use is set to true, step 218. Similarly, if liquid fuel was used during the currently processed minute, step 220, then the logical variable for liquid fuel is set to true, step 222. If both fuels were used at the same or different times during the day, step 224, then the status bit for both fuels in the district status word is set to true, step 228.

The system checks in the SOC/flag arrays for whether the device was online at any time during the currently processed minute, step 230. If so, then the District status bit representing device off line entire day is set to false, step 232.

The system checks the SOC/flags arrays for whether there was a power failure, step 234, communication failure, step 236, or if there was maintenance, step 238, during the currently processed minute. If so, the device down bit is set for the district status word, step 240.

The system checks the SOC and FLAG arrays for whether there was a calibration failure during the currently processed minute, step 242. If there was a calibration failure, then the CEMS out of control bit is set in the district status word, step 244.

Next, six one minute data sums and six valid-observation counters are set to zero, steps 246–248. The counters are for diesel flow, natural gas flow, NOx concentration, oxygen concentration, natural gas pressure, and natural gas temperature. A counter j set in step 246 is incremented by one, step 250. The system checks for whether j exceeds the total number of observations per minute, step 252. If not, then the current observation is within the minute currently being processed, so then the system checks for whether the values for NOx concentration and oxygen concentration for the jth observation are within legally established limits read in step 204, that is, within a certain % of span up from zero or another % down from span, span being the common terminology used in the industry to represent the upper limit of the range of measurement made by an analytical instrument. In accord with AQMD regulations, the NOx or oxygen values that are less than 10% of span may be readjusted to 10% of span, steps 254–256, and 262. If the concentrations were less than 5% of span and the device was not running, steps 256–258, then the values are set to zero, step 260. Adjustments to the concentration values are made in an array called QUALS which contains the data read from the stack data file (5-second data in the present embodiment). The stack data file, representing raw data, is itself never changed. The significance of 5% and device off indicators in the event log file relate to the District's definition of a device being non-operated. There is a signal provided to the computer and logged in the event log as a device stop message (as discussed earlier). But the District says that even if a signal has indicated the monitored device is down (off), they consider it still operating if the NOx in the stack remains above 5% of span. So if the event log indicates a device stop signal and NOx is also below 5%, it is legitimate to set whatever the NOx actually is (below 5%) to exactly zero. For example, suppose NOx span is 2000 ppm. Then if the device is off and NOx is below 0.05×2000=100 ppm (for example 65.34 ppm), then the 65.34 ppm is changed to 0.00 ppm in QUALS array for the relevant 5 second period. If the values were reset to 10% of span in the QUALS array, then a bit so indicating is set in the district status word, step 264.

If the NOx concentration for the stack reading for NOx or oxygen exceeds 95% of span, then an array element in the QUALS array for the reading is changed to reflect that the datum is invalid, for example by setting the value to −99.99, steps 266–272.

The system checks to see if the SOC and FLAG arrays indicate conditions that cause invalid data conditions for each 5 second increment, steps 274–284. The conditions include: calibration ongoing, step 274, CEMS out of control (out of control means that there was a failed calibration, i.e., at certain times during the day, the CEMS could not be relied upon to give accurate data) step 276, communication failure, step 278, power failure, step 280, and whether the 5 second increment was during a maintenance period, step 282. If so, the NOx and oxygen elements in the QUALS array are marked as invalid, step 284. Otherwise, the valid data are summed for the current minute being processed and a valid-data counter is incremented so that the average for the 15 minute interval may be calculated, step 286. Processing then moves back to step 206 where the next minute from the stack data file is processed.

If all minutes for the day have been processed, then processing moves to step 288–296 where all 15 minute averages for NOx concentrations for the day are computed. At steps 290–291, if there was no valid NOx calibration during the day, all NOx concentrations are marked as invalid in the QUALS array and none of the 15 minute averages are computed. The system accomplishes this by checking the NOx calibration counter for a non-zero value.

Processing moves to step 298 where the system checks for whether there was a valid oxygen calibration during the day. If so, then all 15 minute averages for oxygen concentrations for the day are computed, steps 300–302.

In steps 304–316, the system checks each 15 minute period to determine whether there was at least one valid measurement for NOx, and for each of the non-NOx variables required to compute stack flow. If there is at least one valid NOx concentration value in the 15-minute period, then a validity flag for the 15-minute period for NOx concentration is set to true, step 310. If there is at least one valid observation for each of the five Non-NOx variables during the 15-minute period, then a stack flow validity flag for the corresponding 15 minutes of records in a stack flow validity array is set to true, step 314.

Next, six one hour data sums and six valid-observation counters are set to zero, step 317. The counters are for diesel flow, natural gas flow, NOx concentration, oxygen concentration, natural gas pressure, and natural gas temperature. An hour-of-day counter is set to zero, step 318, and is incremented by one, step 320. The system checks to see if all 24 hours for the day have been processed (start of loop), step 324. If not, a 15 minute period counter is incremented by 1 (0 to begin with), step 326.

At step 1000, the system determines whether all four 15-minute periods have been considered for the current hour. If not, processing moves to step 1002. If so, the processing moves to step 1014. At step 1002 the system checks if NOx concentration data for the current 15-minute period is valid, having been set earlier in program. If so then processing moves to step 1004. If not, processing moves to step 1008.

In 1004, the system adds NOx concentration for this 15-minute period to the sum for the hour. At step 1006, the current 15-minute period being valid, the system increments the counter for valid 15-minute periods per hour by one. At step 1008, the system checks to see if all five variables required for computing stack flow are valid for the current 15-minute period. These are diesel flow, natural gas flow, natural gas pressure, natural gas temperature, and oxygen concentration. If so, processing moves to step 1010. If not, processing moves back to step 326 to increment the 15-minute period by one.

At step 1010, the system adds the 15-minute averages for the five stack flow variables to their respective sums. At step 1012, the system increments the count by one for valid 15-minute periods for each of the five variables required to compute stack flow. Processing moves back to step 326.

At step 1014, all four 15-minute periods have been processed to determine validity and, for those that are valid, their data have been added to their respective hourly sums. The system sets a variable counter to zero, and then increments it by one, step 1016 (beginning of loop). At step 1018, the system checks for whether there are four valid 15-minute periods for the currently processed variable. By South Coast Air Quality Management District Rule 2012 ("R2012"), if there are four valid 15 minute periods, then the current hour is a valid hour of data for that variable, and processing moves to 1028. If not, processing moves to step 1020. Even if there are not four valid 15-minute periods, per R2012, the hour may still be valid if this is one of no more than four maintenance/calibration hours per day, and if there are at least two valid 15-minute periods per hour in such maintenance/calibration hour. If NOx is the current variable being processed, step 1020, then processing moves to—step 1022. If not, then processing moves to step 1024.

At step 1022, the system initially sets a NOx concentration validity flag to false for the currently processed hour. At step 1024, the system initially sets an hourly validity flag for stack flow to false. At step 1026 the system checks for whether there are at least two valid 15-minute periods for the current hour. If so, then processing moves to step 1028. If not, then processing moves to step 1032.

At step 1028, the system iterates over the four 15 minute periods for the currently processed hour. There are either four valid 15-minute periods for this hour, or there are at least two of such valid 15-minute periods and this is a maintenance/calibration hour. In either case, the system adds the 15-minute average for each valid 15-minute period (2, 3, or 4 of them) for this variable to its sum. The system also increments the valid 15-minute counter by one for each valid 15-minute period.

At step 1030 the system divides the hourly sum for the variable by the number of 15 minute periods that were used to get that sum. This gives the hourly average for the variable for those hours where there are four valid 15-minute periods as well as those where there were only two or three such valid 15-minute periods per hour, which hour may be reinstated as valid later in the program if it is determined this is an acceptable maintenance/calibration hour.

In step 1032, the system checks for whether all six variables have been processed. If so, then processing moves to step 1034. If not, then processing moves to step 1016.

At step 1034, the system checks for whether there were four valid 15-minute periods in the hour currently under consideration. If so, then processing moves back to step 320 to increment the currently processed hour to the next hour of the day. Otherwise, processing moves to step 1036.

In step 1036, control being transferred here means there were at least two, but fewer than four, valid 15-minute periods for the current hour, and that fewer than four of the allowable maintenance/calibration hours for the day have been used up so far. In step 1038, the system initializes (or increments) the counter for special operating conditions, such as maintenance and calibration periods. In step 1040, the system checks for whether all special operating conditions for the currently processed day have been examined. If not, the processing moves to step 1042. If so, then processing moves back to step 320.

At step 1042, all special operating conditions for this day have not been processed, and the system checks for whether the first (or next) special operating condition is a maintenance or calibration period. If not, the processing moves back to step 1038. If so, then processing moves to step 1044.

At step 1044, if the special operating condition is indeed a maintenance or calibration period, the system checks to see if it occurs during the current hour. If not, processing moves to step 1038 and the SOC counter is incremented. If so, processing moves to step 1046. At step 1046, the system checks for whether four maintenance hours already have been accounted for in accepting as valid, hours with two or three valid 15-minute periods. If so, then no more maintenance hours in which there are fewer than four valid 15-minute periods may be considered valid, and the system breaks out of the current section of code which reinstates hourly validity coinciding with valid maintenance periods, and processing moves to step 1070. If not, then more maintenance periods can occur during valid hours for this day; and processing moves to step 1048.

At step 1048, the system initializes a logical flag, LNQ, to false. At step 1050, the system checks for whether the NOx hourly validity flag is false. If not, processing moves to step 1058 to consider the other five (stack flow) variables. If so, then processing moves to step 1052.

At step 1052, the system checks for whether there were at least two valid 15-minute periods. If not, the processing moves to step 1058. If so, then processing moves to step 1054. At step 1054, there were at least two valid 15-minute periods in the hour, so the system resets the hourly validity flag for NOx concentration to true. At step 1056, one maintenance hour is consumed by reinstating the validity of NOx concentration. To track this, but to avoid double counting if the other five variables also have two or three valid 15-minute periods and will therefore consume a maintenance hour of four available, the system sets LNQ to true. At step 1058, the system checks to see if the stack flow for the current hour is invalid. If not, the processing moves to step 1066. If so, processing moves to step 1060.

At step 1060, the system checks for whether there were, in the current hour, at least two valid 15-minute periods for each of the five variables that go into computing stack flow. If so, then processing moves to step 1062. If not, then processing moves to step 1066. In step 1062, LNQ is set to true. This way, LNQ is false unless, for this hour and because maintenance was occurring, the validity of the hour for NOx concentration, for stack flow, or for both, was reinstated. At step 1064, the stack flow validity flag is set to true for this hour. In step 1066 the system checks for whether LNQ is set to true (is this a consumed maintenance/calibration hour?). If so, processing moves to step 1068. If not, processing moves back to step 1046. At step 1068, one maintenance/calibration hour has indeed been consumed, so the MPC is incremented, which is the maintenance-periods-consumed counter.

If all hours of the day have been processed, step 324, then processing moves to step 1070. At step 1070, either four maintenance hours have been consumed or all 24 hours of the day have been processed. In either case, and after reinstating hourly validity in view of maintenance/calibration hours, the system checks to see if there are still some hours that are invalid. If not, processing moves to step 1084; otherwise, processing moves to step 1072. At step 1072, the system sets bit one of the District status word to false, which indicates that valid data were not obtained all day. At step 1074, the system initializes a counter for 15-minute periods to zero. At step 1076, the system increments by one the counter established in item 1074.

At step 1078, the system checks for whether the hour is valid which contains the current 15-minute period (per counter established in item 1074). If so, then processing moves back to step 1076. If not, then processing moves to step 1080. At step 1080, the hour is not valid, and the system resets to zero the count for the number of observations less than 10% of span that were set to 10% for this 15-minute period. The District requires a count of the number of observations per 15-minute period where a value less than 10% of span was equated to the 10% value. This count was established earlier in the program for each 15-minute period of the day. This step corrects the count since, if the hour's data were invalid, the data are not, in fact, reported at 10%.

At step 1082, the system checks for whether all 15-minute periods have been processed for the day If not, then processing moves to step 1076. If so, then processing moves to step 1084. At step 1084, the system checks for whether the currently processed day is the third day of three to be processed. If not, then processing moves to step 118, to begin reading sub-minute data for the next day. If so, processing moves back to step 1086.

In step 1086, the system initializes an hour counter to zero. In step 1088, the system increments the hour counter by one. In step 1090, the system checks to see if all 62 hours of one three-day period have been processed. If so, the processing moves to step 1100. If not, then processing moves to step 1092. Note—the 62 hours represent 24+24+14 hours; data to be transmitted by 5 pm on day 3, so processing is assumed by this program to occur at 2 pm of day 3, corresponding to 14 hours, allowing time to, remedy problems with data processing or transmission before the 5 pm deadline.

At step 1092, all 62 hours have been processed and the data must be further manipulated to complete calculations. The system checks for whether the hourly validity flag for stack flow for this hour is set to true (valid stack flow). If so, processing moves to step 1094. If not, processing moves to step 1088. At step 1094, fuel gas flow in the raw data are assumed by the flow meter to be measured at a constant reference pressure and temperature that is input to the meter when it is initialized and, based on those reference conditions, flows are converted to standard temperature and pressure (STP). To the extent the actual pressure and temperature deviate from the reference values, the system makes corrections so that the reported values really do represent STP conditions.

At step 1096, the system computes stack flow for the hour due to combustion of natural gas (or other gaseous fuel) per an equation supplied in R2012. At step 1098, the system computes stack flow for the hour due to combustion of diesel (or other liquid fuel) per an equation supplied in R2012, and processing moves to step 1088 to increment the hour counter. At step 1100, all 62 hours have been processed to compute stack flows due to natural gas and diesel combustion. The system sets a switch (IS) to one and processing moves to step 1119.

Next, the system begins the data substitution process in which any hour of invalid data is replaced per protocol laid out in R2012. Because IS switch is set to 1, the system performs an evaluation of the missing data periods and determines for which hours both NOx and stack flow are both missing (invalid). Where both are invalid, OVRLAP will be set to true. This evaluation must be done only once, and IS will be changed to 2 once this first evaluation of all of the missing data periods is completed. When IS is other than 1, the overlap analysis is not needed and not performed. At step 1142, the system begins a two-pass loop to consider NOx concentration (j=1) and then stack flow (j=2). At step 1144, the system initializes at zero a counter for the number of missing data periods (maximum 12 per day or 31 per 3-day processing period of 62 hours) for NOx concentration and a similar counter for missing stack flow data.

At step 1146, the system loops through 62 hours for the three day period. At step 1148, the system checks for whether this the first pass through the NOx/stack flow loop. If so, processing moves to step 1150. At step 1150, the system checks for whether IS is equal to one (is this the first pass through this data substitution algorithm?) If so, processing moves to step 1152. If not, processing moves to step 1160. At step 1152, the system initializes an hourly element of OVRLAP to false. OVRLAP is a logical variable used to track which hours have both NOx concentration and stack flow data missing, as opposed to only one or the other. At step 1154, for the current hour, the system checks for whether both NOx and stack flow data are invalid. If so, processing moves to step 1156. If not, processing moves to step 1160. At step 1156, both NOx and stack flow are invalid. The system sets OVRLAP for this hour to true.

At step 1160, the system checks to see if this hour is the start of a missing data period. That is, is the last hour valid but this hour not? If so, the processing moves to step 1162. If not, processing moves to step 1174. At step 1162, the system checks for whether NOx is being considered (j=1). If so, the processing moves to step 1164. Otherwise, processing moves to step 1172. At step 1164, the system establishes that this is the beginning of a period of missing NOx data. At step 1166, since this is the beginning of a missing NOx data period, the system increments the NOx missing data period counter by one. A missing data period can be from 1 to 62 hours, and this counter ranges from 0 to 31.

At step 1172 the system processes the pass through the loop for stack flow (j=2). The system establishes this hour as the beginning of a period of invalid stack flow data. At step 1170, the system increments by one the count of missing data periods for stack flow. At step 1168, the system terminates the loop for hours.

At step 1174, the system checks for whether the current hour is valid but the last hour not valid. If so, then processing moves to step 1176. If not, the loop termination is reached, step 1168. Otherwise, at step 1176, the system establishes this as the end of a period of missing NOx or stack flow for j=1 or j=2, respectively. Processing then moves to step 1173, which begins a loop over the number of initial or remaining unsubstituted missing data periods. At step 1175, the system checks to see if both NOx and stack flow are missing for the currently processing period. If so then processing moves to step 1177 where the lesser of percent data availability between NOx and stack flow is selected. If the answer to step 1175 was no, then processing moves to step 1178.

At step 1178, the system checks to see if percent data availability is at least 95%. R2012 establishes data substitution requirements largely based on percent data availability. The lower the availability (within the narrow range of 90–100%), the more severe the data substitution requirement. If percent data availability is at least 95%, then go to item 1180; otherwise, processing moves to step 1202. At step 1180, the system checks for whether 1N Bypass is set to true. If so, bypass 1N substitution is processed by processing step 1186. If not, processing moves to step 1182. At step 1182, the algorithm is in an early pass and is set to attempt 1N substitution after every case where any kind of data substitution has occurred, provided that the percent data availability is at least 95% as per R2012. The term 1N refers to some period of N missing hours. Substitution requires the averaging of an equal period of valid hours before and after the missing period, and use of that average as the substitute value for the missing hours. Another requirement to permit 1N substitution is that the missing data period not exceed 24 hours. If this is not the case, processing moves to step 1184. If it is the case, then 1N data substitution is not permitted, and the system bypass the processing it by moving to step 1186.

At step 1184 the system checks for whether there the requisite 1N hours of valid data before and after the missing data period (true zero values are allowed). If so, processing moves to step 1210. Otherwise processing moves to step 1220. At step 1210, the system computes the average of 1N hours before, and 1N hours after the missing data period for NOx or stack flow according to which pass through the loop is set by step 1169. At step 1212, the system sets IS to 2. The switch setting will prevent OVRLAP from being reset unnecessarily. At step 1214, the system substitutes the 1N average value computed in item 1210 for the missing data period. At step 1216, the system marks the missing data period as having been substituted to prevent repeated substitutions later and improper use of substitute data in determining daily maxima (the maxima are derived only from valid data). The system performs the marking by using a three-character code in an array called DS. Before data substitution is performed, each DS element is set to blank for all three characters. When data substitution occurs, a non-blank three-character code is placed into DS for the particular hour. The first character represents the percent data availability based on the hours of on-line availability of the NOx or oxygen analyzer and the monitored device over the prior 365 days. The second character represents the data substitution algorithm used for the hour under consideration. The third character indicates whether data substitution is for NOx concentration, stack flow, or NOx mass emission rate. Setting an element of DS to non-blank constitutes a marker indicating that data substitution has occurred.

Processing moves back to step 1142.

If the decision in step 1184 resulted in a no answer, then processing moves to step 1220 which designates the end of the missing data period loop.

At step 1222, the system checks for whether any data substitutions resulted from the pass through the MDP loop just concluded. If not, processing moves to step 1224. If so, processing moves to step 1234. At step 1224, the system checks for whether any missing data periods remain. If so, processing moves to step 1226; otherwise, processing moves to step 1230. At step 1226, The system checks for whether the 1N Bypass is set (is the variable set to true). If so, this means that 1N was already bypassed but the algorithm could still not complete data substitution. If this is so, then the system writes an error message to the monitor and terminates processing. Manual intervention may be required. If the 1N Bypass was not set, then processing moves to item 1228. At step 1228, the system sets the 1N Bypass logical variable to true so that subsequent attempts to perform data substitution will not include 1N. This will force the 30-day maximum to be used (or 365-day etc.) because repeated attempts at 1N substitution were unsuccessful. Processing move to step 1173 to restart the loop that steps through missing data periods.

At step 1230, there are no more missing data periods remaining for NOx concentration if this was the first pass through the NOx/stack flow loop. If it was the second pass, then data substitution for stack flow is complete. In the former case, processing moves to the start of the loop at step 1169, and the loop index is incremented so that stack flow will be processed. In the latter case, processing moves to step 1236.

At step 1234, the last pass through the data substitution loop was successful, i.e., substitution occurred for one or more missing data periods. Because the 1N Bypass may have been set to true, the system resets it to false so that 1N can be attempted again for the remaining missing data. The system re-enters the missing data period loop of step 1173.

At step 1236, the data substitution for NOx concentration and stack flow are now completed. The system enters a loop through 62 hours. At step 1238, the system checks to see if OVRLAP is true for this hour. If not, processing moves to step 1240. If so, then processing moves to loop terminator and the system either increments the loop counter or moves to step 1300.

At step 1240, the system computes hourly NOx mass emissions for valid and substituted data where either NOx concentration or stack flow was missing, but not where both were missing (i.e., where OVRLAP is true). Processing moves to the loop terminator and the system either increments the loop counter or processing moves to step 1300.

At step 1300, the system loops through 62 hours. At step 1302, the system sets the number of missing NOx mass emission rates (i.e., where both stack flow and NOx concentrations are missing, NOx mass emission rate substitution is required under R2012) to zero. At step 1304, for the currently processed hour, the system checks for whether OVRLAP is true (i.e., are both NOx concentration and stack flow missing). If so, processing moves to step 1306. If not, processing moves to step 1318. At step 1306, the processed hour is one in which both NOx concentration and stack flow are missing. The system checks for whether a missing data period was on-going last hour. If so, then the currently processed hour is not the start of a missing data period. The loop terminates at step 1312.

If the last hour was not a missing data period, then, at step 1308, this is indeed the beginning of a missing data period in which NOx mass emission must be substituted. At step 1310, the system increments the missing data period counter. The system increments the loop index and returns to step 1300 to pass through the loop again. But if all hours have been considered, then processing moves to step 1314.

At step 1314, after all 62 hours have been considered and all missing data periods requiring NOx mass emission substitution have been characterized (start and stop hours for each) and counted, the system selects the lesser percent data availability, as required under R2012, between NOx concentration and oxygen (stack flow). At step 1316, the system sets the 1N Bypass to false.

If the OVRLAP was false for a processed hour, step 1318, that means the hour is not part of an MDP requiring NOx mass emission substitution, the system checks for whether a missing data period was on-going last hour. If so, then processing moves to step 1320. If not, then processing moves to step 1312. At step 1320 the hour is not part of a missing data period but the last hour was, in which case the system establishes the last hour as the end of the most recent missing data period.

At step 1322, the system loops through the number of missing data periods for NOx mass emission rates. At step 1324, the system checks if the percent data availability is at least 95%. If so, processing moves to step 1326. If not, processing moves to step 1370. At step 1326, the system checks for whether 1N Bypass set to true. This implies that the algorithm was attempting to do 1N substitution, failed, and no substitutions occurred during that attempt even though some missing data periods remain. If so, then processing moves to step 1368. If not, processing moves to step 1328. At step 1328, the system checks for whether there are more than 24 missing hours. If so, 1N processing is not applicable; and processing moves to step 1350. If not, processing moves to step 1330.

At step 1330, the system checks for whether there are 1N valid NOx mass emission values both before and after the missing data period. If so, then processing moves to 1344. If not, processing moves to step 1332. At step 1332, the system loop terminator is reached. The system increments the loop index, tests it to see if it is greater than the number of missing date periods, and if not, the system passes through the loop again or, if so, processing moves to step 1334.

At step 1334, the system checks for whether there was data substitution done this pass through the loop. If so, processing moves to step 1336. If not, processing moves to step 1338. At step 1336, the system sets 1N Bypass to false so that, regardless of the kind of data substitution that occurred last pass through the missing data period loop, 1N will be attempted next pass. The system then re-enters the missing data period loop at step 1322.

At step 1338, the system checks for whether there are any missing data periods remaining. If not, then processing moves to step 1378. If so, then processing moves to step 1340. At step 1340, the system checks for whether 1N Bypass set to true. If so, then there is a processing error. Processing moves to step 1384 in that case. If not, processing moves to step 1342. At step 1342, the system sets 1N Bypass to true and re-enter the missing data period loop at step 1322.

At step 1344, the system computes the average of 1N NOx mass emission values before and after the missing data period. At step 1346, the system substitutes the average computed in item 1344 for each missing data value. At step 1348, the system marks the substituted data using the DS array so that it will not be substituted again and so that it will be ignored when daily maxima are identified. At step 1350, the system checks for whether a valid 30-day maximum for NOx mass emission rate. If so, processing moves to step 1352. If not, processing moves to step 1354. At step 1352, the system selects the 30-day maximum and processing moves back to step 1364. At step 1354, the system checks for whether there is a valid 365-day maximum. If so, then processing moves to step 1356. If not, then processing moves to step 1358. At step 1356, the system selects the 365-day maximum and processing moves to step 1364.

At step 1358, the system checks for whether there is a valid lifetime maximum. If so, processing moves to step 1360. If not, processing moves to step 1362. At step 1360, the system selects the lifetime maximum and processing moves to step 1364. At step 1362, the system selects the uncontrolled maximum emission rate for the device as specified under R2012. At step 1364, the system performs data substitution for this missing NOx mass emission data period using the 30-day maximum of step 1352, the 365-day maximum of step 1356, or the lifetime maximum of step 1360. Processing moves to step 1348.

At step 1368, the system checks for whether there were more than 24 hours missing. If so, then the 30-day maximum is not applicable. Processing moves to step 1354 to see if there is a 365-day maximum available. If 24 or fewer hours are missing, processing moves to step 1350.

At step 1370, the system checks for whether the percent data availability is less than 90%. If so, processing moves to step 1360. If not, processing moves to step 1372. At step 1372, the system checks for whether there are more than 3 hours missing. If not, and since the percent data availability is less than 95% but is at least 90%, then processing moves to step 1374. If more than 3 hours are missing, then processing moves to step 1368.

At step 1374, the system checks for whether the hour before, and the hour after, the missing data period are non-zero. If not, processing moves to step 1368. Otherwise processing moves to step 1376. At step 1376, the system averages the non-zero NOx mass emission rate immediately before the missing data period with the non-zero value immediately after. Processing moves to step 1348 to do the data substitution.

At step 1378, the system write the maxima for the day, for NOx concentration, natural gas stack flow, diesel stack flow, natural gas NOx mass emission rate, and diesel NOx mass emission rate, excluding substituted values, to a direct access file storing the maxima data. Processing moves back to step 102.

At step 1380, the system writes hourly and 15-minute reports to provide all documentation required under R2012. At step 1382, the system prepares transmission files as required by R2012. At step 1384, the system writes an error message to the monitor and terminate processing. There is an error in data substitution and manual intervention is required in this case.

At step 1120, the system enters a loop to step backward in a direct-access file, starting yesterday, through all prior days of CEMS operation back to the original CEMS certification. At step 1122, the system reads, from the historical record specified by the loop counter of step 1120, the daily maximum for the current device of NOx concentration, stack flow due to natural gas combustion, stack flow due to diesel combustion, the NOx mass emission rate due to natural gas combustion, and the NOx mass emission rate due to diesel combustion. Also, the system reads the number of on-line hours for the CEMS NOx analyzer, the CEMS oxygen analyzer, and the monitored device itself (e.g., NOx emitting engine, boiler, turbine). At step 1124, the system checks for whether the record just read represents a day fewer than 366 days back from yesterday. That is, is it within the duration of a year ending yesterday? If so, processing moves to step 1126. If no, then processing moves to step 1132.

At step 1126, the time period is within 365 days ending yesterday. The system increments the total of on-line hours for the NOx analyzer, oxygen analyzer, and monitored device by the corresponding number of on-line hours for the record just read. At step 1128, the system checks to see if this pass is for yesterday. If so, processing moves to step 1130. If not, processing moves to step 1132.

At step 1130, the pass represents yesterday. The system tentatively sets the 30-day, 365-day, and lifetime maxima for NOx concentration, stack flow due to natural gas combustion, stack flow due to diesel combustion, NOx mass emission rate due to natural gas combustion, and NOx mass emission rate due to diesel combustion equal to yesterday's corresponding maxima.

At step 1132, the case is handled where the current pass is not for yesterday. The system compares this day's maxima with those tentatively stored, and replaces any tentatively stored value if that stored value is the lower of the two. At step 1134, the system checks for whether it is the $30^{th}$ prior day (29 days before yesterday). If so, processing moves to step 1136. If not, processing moves to step 1138. At step 1136, it is indeed the 30$^{th}$ prior day, so the system sets the 30-day maxima for NOx concentration, natural gas stack flow, diesel stack flow, natural gas NOx mass emission rate, and diesel NOx mass emission rate to the corresponding tentatively stored values. At step 1138 check to see if it is 365$^{th}$ prior day. If it is, processing moves to step 1140. If not, processing moves to step 1141. At step 1140, it is the 365$^{th}$ prior day, and the system sets the 365-day maxima equal to the tentatively stored values, with same sense as in step 1136.

At step 1141, the end of loop begun in item 1120 is reached, and the system returns control there until loop index is exceeded. Control is transferred to item 1102 once the loop terminates (once all historical daily maxima have been read and considered). At step 1102, the system sets the lifetime maxima to the tentatively stored values with same sense as in step 1136. At step 1104, the system checks for whether there were fewer than 365 days to consider. If so, processing moves to step 1106. If not, processing moves to step 1112. At step 1106, the system sets 365-day maximum equal to the lifetime maximum. At step 1108, the system checks for whether there were fewer than 30 days to consider. If so, processing moves to step 1110. If not, processing moves to step 1112. At step 1110, the system sets the 30-day maximum equal to lifetime maximum. At step 1112, the system finds percent data availabilities by dividing the prior 365 days (or fewer days if historical data do not go back that far) of total on-line NOx analyzer hours by the total on-line hours for the monitored device. The system does the same for the oxygen analyzer. This can legitimately (per the District) yield percent data availabilities over 100%.

At step 1114 the 1N Bypass is set to false. The logical variable represented by 1N Bypass causes the first pass through data substitution to attempt to use 1N substitution. Once data substitution for any missing data period has occurred using any of the available substitution protocols, the program algorithm resets, and again attempts to use 1N substitution. This can potentially lead to a failure to perform all data substitutions with the program entering an infinite loop attempting to do 1N substitution. The 1N Bypass variable avoids this.

At step 1169, the system begins a 2-pass loop to consider NOx concentration first and then stack flow. At step 1171, the system selects percent data availability for NOx or for stack flow depending on whether this is the first or second pass through the loop of step 1168. At step 1173, the system begins to loop through the number of missing data periods. At step 1175, the system checks for whether the current period is a period in which both NOx and stack flow are missing (OVRLAP=true). If so, processing moves to step 1177. Otherwise, processing moves to step 1178.

With the above description in mind, an example embodiment will now be described to illustrate one possible implementation of the present invention. Since the requirement for real-time monitoring of stack gas pollutants emitted from industrial facilities is now commonplace, the physical approach is usually the installation of a CEMS, including a DAS and an RTU for acquiring, processing, and electronically transmitting the emissions data to a receiving station such as a local air pollution control authority.

The DAS of one embodiment of the present invention can be source code written in a high level programming language, for example FORTRAN-77, C, or C++. The software is preferably designed to perform all computations and data manipulations necessary to accept CEMS and other equipment digital data and prepare output mass emission files in the form required by the regulatory agency. Such mass emissions may be of NOx (oxides of nitrogen), CO (carbon monoxide), Sox (oxides of sulfur) or any other gaseous pollutant for which mass emissions must be computed.

In one embodiment a single implementation (execution) of the program can accommodate up to three physical emitting devices (e.g., engines, boilers, turbines, furnaces), although any number of physical devices can be accommodated by multiple (sequential) executions of the present embodiment, or the program could have been written to accommodate any larger or smaller number of physical devices without any change to the novel features of the invention.

The three devices accommodated in a single execution of the present embodiment of the invention require three devices internal to the program ("DAS devices"). Any one DAS device can be associated with any one of the three physical devices (e.g., engines). For example, if an industrial facility has three CEMS, one associated with a boiler, one with an engine, and one with a furnace, DAS Device One might be associated with the engine, DAS Device Two with the furnace, and DAS Device Three with the boiler. Any other combination is equally acceptable.

In another type of application, the DAS can be used in a cogeneration facility. For example, such facility might have two physical devices requiring CEMS—a gas turbine (e.g., driving a chiller) with waste turbine-heat recovery used to generate electric power via a steam turbine and generator. When the amount of steam produced with waste heat is inadequate to accommodate the electric power demand (load), duct burners are available (physically located in the engine exhaust duct) to provide supplemental heat for production of steam.

In an installation where the duct burner exhaust pollutants are monitored separately from that of the engine, the DAS can be used in its simplest configuration, namely, the engine is represented by one DAS device and the duct burner by a second DAS device. This leaves one DAS device unused. In some such installations, however, the duct burner exhaust is directly and immediately combined with the turbine exhaust, and there is no way to directly measure the composition of the duct burner exhaust. This may be because the burners are physically located inside the turbine exhaust duct or because the duct burner exhaust duct is not amenable to sampling. In this situation, there may be NOx and oxygen analyzers monitoring the exhaust directly downstream of the turbine (Location One Analyzers) and another pair of analyzers (Location Two Analyzers) monitoring the combined exhaust downstream of the duct burners (i.e., monitoring the combined duct burner and turbine exhausts). An additional level of complexity may result from the existence of main and secondary exhaust stacks.

Under some circumstances, there may be an additional level of complexity due to the need for a secondary stack. It may be necessary to divert the turbine exhaust to that secondary stack, the main stack being used for duct burner exhaust alone, both turbine and duct burner exhaust may go to the main stack during some part of the time when both are operating, the turbine alone may vent to the main stack (duct burner inoperative), or part of the turbine exhaust may be diverted to the secondary stack when the turbine alone provides more than enough heat for electric power generation. In this situation, information (device status signal) is provided at each sampling time to the DAS by the physical system, regarding on-off status of the turbine and of the duct burner, and regarding where the turbine exhaust is being vented (i.e., the main or secondary stack).

In this situation where the duct burner exhaust cannot be directly monitored, regulatory requirements may make it unacceptable from a regulatory standpoint to mathematically separate the two exhausts in the raw data even where the inherent nature of the data themselves would allow it, or it may be physically impractical or impossible to correctly do so. In such cases, the DAS devices may be configured to analyze the combined exhaust of the engine and duct burners and compute the required mass emission rates. For example, DAS Device One may be assigned directly to the turbine, and it analyzes the exhaust of the turbine alone, whether that is directed to the main or secondary stack. DAS Device Two applies only to the turbine when its exhaust is directed to the main stack. DAS Device Three represents the main stack itself. Then, to obtain duct burner emissions, DAS Device Two (turbine only when directed to the main stack) is subtracted from DAS Device Three (turbine plus duct burners if operating), resulting in quantification of the mass emissions from the duct burners alone.

While the particular systems and methods herein shown and described in detail are fully capable of attaining the above described objects of this invention, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A computer implemented method for processing air quality management emissions information, the method comprising:

receiving a plurality of emissions data from an exhaust pathway sensor, each emissions data correlating to a unique time;

storing the plurality of emissions data in a data storage area;

processing the plurality of emissions data to generate a quantified emissions data value correlating to a time range encompassing a plurality of unique times;

storing the quantified emissions data value in the data storage area; and providing the quantified emissions data value to an air quality management district.

2. The method of claim 1, wherein the emissions data received from the exhaust pathway sensor is received via a wireless communication link.

3. The method of claim 1, wherein the emissions data is received from the exhaust pathway sensor as often as every minute.

4. The method of claim 1, wherein the emissions data received from the exhaust pathway sensor comprises analog signals, the method further comprising the step of converting the analog signals to digital signals prior to storing the emissions data in the data storage area.

5. The method of claim 1, wherein the processing step further comprising the steps of:

identifying a plurality of elements, each element corresponding to a special operating condition and a unique time;

storing each element in the plurality of elements in the data storage area; and processing a plurality of stored elements corresponding to a particular special operating condition and a range of time comprising a plurality of unique times to generate a status for the particular special operating condition; and storing the status for the particular special operating condition in the data storage area.

6. A system for processing air quality management emissions information, the system comprising:

a sensor device adaptable to collect emissions data from an exhaust pathway;

a programmable logic control device communicatively coupled with the sensor device and adaptable to receive emissions data from the sensor device;

a data storage area communicatively coupled with the programmable logic control device, the data storage area adaptable to store emissions data received from the programmable logic control device;

a data acquisition module adaptable to quantify the emissions data and store the quantified emissions data value in the data storage area; and a communication means adaptable to provide the quantified emissions data value from the data storage area to an air quality management district.

7. The system of claim 6, wherein the programmable logic control device comprises an analog to digital converter adaptable to receive analog signals from the sensor device and convert the analog signals to digital signals.

8. The system of claim 6, wherein the programmable logic control device is communicatively coupled with the sensor device via a wireless communication link.

9. The system of claim 6, wherein the programmable logic control device is configured to receive emissions data from the exhaust pathway sensor as often as every minute.

10. A computer readable medium having stored thereon one or more sequences of instructions for causing one or more microprocessors to perform the steps for processing air quality management emissions information, the steps comprising:

receiving a plurality of emissions data from an exhaust pathway sensor, each emissions data correlating to a unique time;

storing the plurality of emissions data in a data storage area;

processing the plurality of emissions data to generate a quantified emissions data value correlating to a time range encompassing a plurality of unique times;

storing the quantified emissions data value in the data storage area; and providing the quantified emissions data value to an air quality management district.

11. The computer readable medium of claim 10, wherein the emissions data received from the exhaust pathway sensor is received via a wireless communication link.

12. The computer readable medium of claim 10, wherein the emissions data is received from the exhaust pathway sensor as often as every minute.

13. The computer readable medium of claim 10, wherein the emissions data received from the exhaust pathway sensor comprises analog signals, the method further comprising the step of converting the analog signals to digital signals prior to storing the emissions data in the data storage area.

14. The computer readable medium of claim 10, wherein the processing step further comprising the steps of:

identifying a plurality of elements, each element corresponding to a special operating condition and a unique time;

storing each element in the plurality of elements in the data storage area; and processing a plurality of stored elements corresponding to a particular special operating condition and a range of time comprising a plurality of unique times to generate a status for the particular special operating condition; and storing the status for the particular special operating condition in the data storage area.

15. A system for processing air quality management emissions information, the system comprising:

means for receiving emissions data collected from an exhaust pathway;

means for storing the emissions data in a data storage area;

means for compiling the emissions data into a quantified emissions data value;

means for storing the quantified emissions data value in the data storage area; and means for providing the quantified emissions data value from the data storage area to an air quality management district.

16. The system of claim 15, wherein the means for storing the emissions data in a data storage area comprises an analog to digital converter adaptable to receive analog signals and convert the analog signals to digital signals.

17. The system of claim 15, wherein the means for receiving emissions data comprises a wireless communication link.

18. The system of claim 15, wherein the means for receiving emissions data is configured to receive emissions data as often as every minute.

19. A computer implemented method for processing air quality management emissions information, the method comprising:

receiving a plurality of emissions data from an exhaust pathway sensor, each emissions data correlating to a unique time;

storing the plurality of emissions data in a data storage area;

processing the plurality of emissions data to generate a quantified emissions data value correlating to a time range encompassing a plurality of unique times, wherein the processing step comprises:

identifying a plurality of elements, each element corresponding to a special operating condition and a unique time, wherein the special operating conditions comprise device stopped, calibration ongoing, general calibration failure, power failure, communication failure, analyzer span calibration failure, and analyzer zero calibration failure;

storing each element in the plurality of elements in the data storage area;

processing a plurality of stored elements corresponding to a particular special operating condition and a range of time comprising a plurality of unique times to generate a status for the particular special operating condition; and storing the status for the particular special operating condition in the data storage area;

storing the quantified emissions data value in the data storage area; and providing the quantified emissions data value to an air quality management district.

20. A computer readable medium having stored thereon one or more sequences of instructions for causing one or more microprocessors to perform the steps for processing air quality management emissions information, the steps comprising:

receiving a plurality of emissions data from an exhaust pathway sensor, each emissions data correlating to a unique time;

storing the plurality of emissions data in a data storage area;

processing the plurality of emissions data to generate a quantified emissions data value correlating to a time range encompassing a plurality of unique times, wherein the processing step comprises;

identifying a plurality of elements, each element corresponding to a special operating condition and a unique time, wherein the special operating power failure, communication failure, analyzer span calibration failure, and analyzer zero calibration failure;

storing each element in the plurality of elements in the data storage area;

processing a plurality of stored elements corresponding to a particular special operating condition and a range of time comprising a plurality of unique times to generate a status for the particular special operating condition; and storing the status for the particular special operating condition in the data storage area;

storing the quantified emissions data value in the data storage area; and providing the quantified emissions data value to an air quality management district.

* * * * *